US012053332B2

(12) United States Patent
Voigt et al.

(10) Patent No.: US 12,053,332 B2
(45) Date of Patent: Aug. 6, 2024

(54) METHOD FOR OPERATING A SURGICAL MICROSCOPY SYSTEM, AND SURGICAL MICROSCOPY SYSTEM

(71) Applicant: Carl Zeiss Meditec AG, Jena (DE)

(72) Inventors: Christian Voigt, Abtsgmuend (DE); Markus Philipp, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 674 days.

(21) Appl. No.: 16/894,799

(22) Filed: Jun. 6, 2020

(65) Prior Publication Data

US 2020/0383747 A1 Dec. 10, 2020

(30) Foreign Application Priority Data

Jun. 6, 2019 (DE) .................. 10 2019 208 287.4

(51) Int. Cl.
 *G02B 21/00* (2006.01)
 *A61B 90/25* (2016.01)
 *G02B 21/24* (2006.01)

(52) U.S. Cl.
 CPC .......... *A61B 90/25* (2016.02); *G02B 21/0012* (2013.01); *G02B 21/24* (2013.01)

(58) Field of Classification Search
 CPC ............ G02B 21/00; G02B 21/0004; G02B 21/0012; G02B 21/0028; G02B 21/24; G02B 7/00; G02B 7/001; A61B 90/25

(Continued)

(56) References Cited

U.S. PATENT DOCUMENTS 6,129,319 A * 10/2000 Metelski ............... G02B 7/001
 359/384
6,539,333 B1 3/2003 Metelski
 (Continued)

FOREIGN PATENT DOCUMENTS

DE 102004063606 A1 7/2006
DE 102016200214 A1 7/2017
 (Continued)

OTHER PUBLICATIONS

Dalin Zhang et al.: EEG-based Intention Recognition from Spatio-Temporal Representations via Cascade and Parallel Convolutional Recurrent Neural Networks; Association for the Advancement of Artificial Intelligence, Aug. 22, 2017, https://arxiv.org/abs/1708.065783.

(Continued)

*Primary Examiner* — Thong Q Nguyen
(74) *Attorney, Agent, or Firm* — Ewers IP Law PLLC; Falk Ewers

(57) ABSTRACT

A method for operating a microscopy system is provided. The microscopy system includes a microscope and a stand supporting the microscope. The microscope is arranged on the stand. The stand includes at least one drive device configured to move the microscope. The method includes determining a specified value or a specified change of a modulable inertia of the microscopy system based on a state variable and/or based on user information and/or based on a force acting on the microscopy system and/or based on a current instance of application. The at least one drive device is controlled such that a divergence between the specified value and an actual value of the modulable inertia is reduced or the modulable inertia is varied in accordance with the specified change.

18 Claims, 5 Drawing Sheets

(58) Field of Classification Search
USPC .................................................. 359/368–389
See application file for complete search history.

(56) References Cited

U.S. PATENT DOCUMENTS

| | | | |
|---|---|---|---|
| 6,786,896 | B1 | 9/2004 | Madhani et al. |
| 7,158,292 | B2 * | 1/2007 | Metelski ................ G02B 7/001 |
| | | | 359/384 |
| 2006/0126167 | A1 | 6/2006 | Piontkowski |
| 2013/0205558 | A1 | 8/2013 | Sporer et al. |
| 2014/0229006 | A1 | 8/2014 | Rümping et al. |
| 2016/0270874 | A1 | 9/2016 | Sporer et al. |
| 2017/0198856 | A1 | 7/2017 | Voigt et al. |

FOREIGN PATENT DOCUMENTS

| | | |
|---|---|---|
| EP | 1326115 B1 | 2/2007 |
| WO | 2006091494 A1 | 8/2006 |
| WO | 2012007168 A1 | 1/2012 |

OTHER PUBLICATIONS

Jones et al. Influence of the mechanical properties of a Manipulandum on human operator dynamics. I. Elastic stiffness, Biological Cybernetics (1990), Chapter 62, pp. 299-307, School of Physical and Occupational Therapy, and Department of Biomedical Engineering, McGill University, Montreal, Canada.

Jones et al. Influence of the mechanical properties of a Manipulandum on human operator dynamics. II. Viscosity, Biological Cybernetics (1993), Chapter 69, pp. 295-303, School of Physical and Occupational Therapy, and Department of Biomedical Engineering, McGill University, Montreal, Canada.

Crommentuijn et al. The Effect of Damping in an Input Device on Human Positioning Performance, C. Stephanidis (Ed.): Posters, Part II, HCII 2011, CCIS 174 (2011), pp. 330-334, Human-Technology Interaction Group, Eindhoven University of Technology, The Netherlands.

Crommentujin et al. The Effect of Coulomb Friction in a Haptic Interface on Position Performance, A.M.L Kappers et al. (Eds.): EuroHaptics 2010, Part II, LNCS 6192, pp. 398-405, Human-Technology Interaction Group, Eindhoven University of Technology, The Netherlands.

Berkelman et al. Effects of Friction Parameters on Completion Times for Sustained Planar Positioning Tasks with a Haptic Interface, ResearchGate, (2006), Department of Mechanical Engineering, University of Hawaii-Manoa.

Keemink et al. Using Position Dependent Damping Forces around Reaching Targets for Transporting Heavy Objects: A Fitts' Law Approach, ResearchGate, Jun. 2016.

Ott, Cartesian Impedance Control of Redundant and Flexible-Joint Robots (Part 1 and Part 2), Springer Tracts in Advanced Robotics (STAR), (2008), vol. 49, Springer-Verlag Berlin Heidelberg.

Duchaine et al. General Model of Human-Robot Cooperation Using a Novel Velocity Based Variable Impedance Control, Second Joint EuroHaptics Conference and Symposium on Haptic Interfaces for Virtual Environment and Teleoperator Systems, (2007), IEEE Computer Society, Department of Mechanical Engineering, University of Quebec Laval, Canada.

Hlaing et al. Variable Admittance Controller for Physical Human Robot Interaction, (2017), pp. 2929-2934, IEEE Computer Society, Mechatronic Engineering Department, Yangon Technological University.

Tsumugiwa et al. Variable Impedance Control Based on Estimation of Human Arm Stiffness for Human-Robot Cooperative Calligraphic Task, International Conference on Robotics & Automation, Washington D.C. (May 2002), pp. 644-650, IEEE Computer Society, Department of Mechanical Engineering, Doshisha University, 1-3 Tatara-Miyakodani, Kyo-Tanabe city, Kyoto pref., 610-0321 Japan.

Jlassi et al. An Online Trajectory Generator-Based Impedance Control For Co- manipulation Tasks, IEEE Haptics Symposium, (2014), pp. 391-396, University Paris-Sud, UMR8506, Orsay, F-91405, CNRS and SUPELEC, UMR8506, LSS, Gif-sur-Yvette, F-91190.

Infante et al. Usability of Force-Based Controllers in Physical Human-Robot Interaction, (2011), pp. 355-361, Lausanne, Switzerland.

Yamada et al. Proposal of Skill-Assist : A System of Assisting Human Workers by Reflecting Their Skills in Positioning Tasks, (1999), pp. 11-16, Toyota Technical Institute, 2-12-1, Hisakata, Tempaku, Nagoya, Aichi, 458-8511, Japan.

Lecours et al. Variable admittance control of a four-degree-of-freedom intelligent assist device, IEEE International Conference on Robotics and Automation, (May 2012), pp. 3903-3908, Department of Mechanical Engineering, University of Quebec, Laval, Canada.

Asada et al. The direct teaching of tool manipulation skills via the impedance identification of human motions, (1988), pp. 1269-1274, Department of Applied Systems Science Kyoto University, Kyoto 606, Japan.

Ikeura et al. Variable Impedance Control of a Robot for Cooperation with a Human, IEEE International Conference on Robotics and Automation, (1995), pp. 3097-3102, Department of Mechanical Engineering, Tohoku University, Aoba, Aramaki-aza, Aoba-ku, Sendai, 980-77, Japan.

Mitsantisuk et al. Variable Mechanical Stiffness Control based on Human Stiffness Estimation, International Conference on Mechatronics, (2011), pp. 731-736, Department of Electrical Engineering, Nagaoka University of Technology, 1603-1, Kamitomiokamachi, Nagaoka, Niigata 940-2188, Japan.

Lee et al. Improving Transparency in Physical Human-Robot Interaction Using an Impedance Compensator, IEEE/ASME Transactions on Mechatronics, vol. 23, No. 6, Dec. 2018.

Maeda et al. Human-Robot Cooperative Manipulation with Motion Estimation, International Conference on Intelligent Robots and Systems, (2001), pp. 2240-2245, Department of Precision Engineering, School of Engineering, The University of Tokyo, 7-3-1 Hongo, Bunkyo-ku, Tokyo 113-8656 Japan.

Corteville et al. Human-inspired robot assistant for fast point-to-point movements, (2007), Department of Mechanical Engineering, University of Leuven, 3000 Leuven, Belgium.

Li et al. Human-Robot Collaboration Based on Motion Intention Estimation, IEEE/ASME Transactions on Mechatronics, vol. 19, No. 3, Jun. 2014, pp. 1007-1014, Social Robotics Laboratory, Interactive Digital Media Institute, and NUS Graduate School for Integrative Sciences and Engineering, National University of Singapore, Singapore 119613.

Ranatunga et al. Intent Aware Adaptive Admittance Control for Physical Human-Robot Interaction, IEEE International Conference on Robotics and Automation (ICRA), (2015), pp. 5635-5640, University of Texas at Arlington Research Institute, Ft. Worth, TX, 76118 USA.

Dimeas et al. Fuzzy Learning Variable Admittance Control for Human-Robot Cooperation, IEEE/RSJ International Conference on Intelligent Robots and Systems (IROS 2014), pp. 4770-4775, Robotics Group, Department of Mechanical Engineering & Aeronautics, University of Patras, 26500 Patra, Greece.

Dimeas et al. Reinforcement Learning of Variable Admittance Control for Human-Robot Co-manipulation, IEEE/RSJ International Conference on Intelligent Robots and Systems (IROS 2015), pp. 1011-1016, Robotics Group, Department of Mechanical Engineering & Aeronautics, University of Patras, 26500 Patra, Greece.

Du et al. Variable Admittance Control Based on Fuzzy Reinforcement Learning for Minimally Invasive Surgery Manipulator, Sensors MDPI Journal, (2017), State Key Laboratory of Robotics and System, Harbin Institute of Technology, 2 Yikuang Street, Harbin 150080, China.

Morizono A Preliminary Study for Realization of Field Impedance Equalizer with an Automatic Adjusting Function, IEEE International Workshop on Robot and Human Interactive Communication, (2004), pp. 407-412, Graduate School of Engineering, Toyota Technological Institute, 2-12-1, Hisakata, Tempaku-ku, Nagoya, 468-8511, Japan.

(56) References Cited

OTHER PUBLICATIONS

Park et al. Human Implicit Intent Discrimination Using EEG and Eye Movement, Neural Information Processing, Conference Proceedings, Part I (2014), pp. 11-18, 21st International Conference, ICONIP 2014, Kuching, Malaysia, Nov. 3-6, 2014.

Siciliano et al. Dexterity Indices, Other Performance Indices, Task-Space Analysis, Springer Handbook of Robotics (2007), pp. 405-408, 710-711, Springer, Berlin, Heidelberg, Germany.

\* cited by examiner

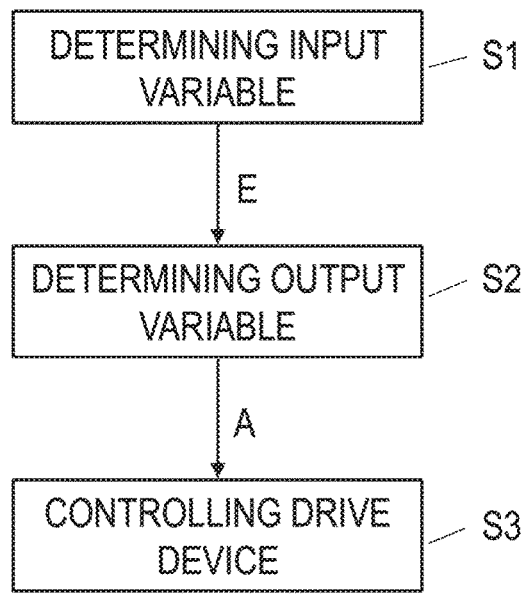
FIG. 1
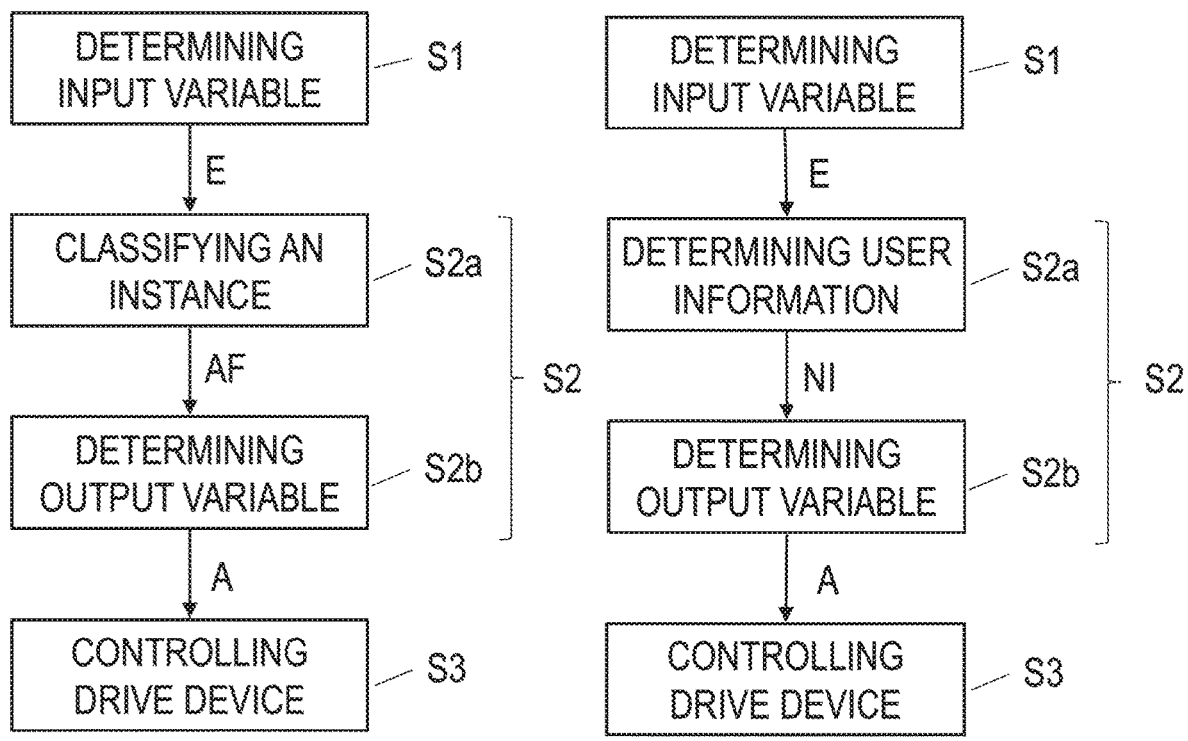
FIG. 2
FIG. 3

METHOD FOR OPERATING A SURGICAL MICROSCOPY SYSTEM, AND SURGICAL MICROSCOPY SYSTEM

CROSS REFERENCE TO RELATED APPLICATIONS

This application claims priority to German patent application DE 10 2019 208 287.4, filed Jun. 6, 2019, the entire content of which is incorporated herein by reference.

TECHNICAL FIELD

The disclosure relates to a method for operating a surgical microscopy system and to a surgical microscopy system.

BACKGROUND

A surgical microscopy system normally includes a microscope and a stand for supporting the microscope, the microscope being arranged on the stand. The stand allows, in particular actuator-assisted, movement of the microscope in space, in particular with multiple, for example up to six, degrees of freedom.

If a user, e.g., when repositioning the microscope, operates the microscope or the microscopy system manually in order to move it in space, the user needs to overcome inertial forces. These inertial forces arise on account of physical laws during the acceleration of massive mechanical structures and oppose a change of speed.

This inertia subjectively results in the user needing to summon up an effort in order to start the stand moving or to decelerate it. In certain instances of application, it may be desirable to reduce these forces for the user, since they are demanding on the user, and thereby to increase a usability of the microscopy system. In particular when the surgical microscopy system is used for long periods, this effort can otherwise lead to fatigue in the user. In other instances of application, however, it may also be desirable to vary this sensed effort, in particular in order to increase safety of operation.

It is a known practice to reduce the inertia of a system with design measures. However, these can lead to reduced efficiency and usability of the system, to lower robustness, to increased manufacturing costs, to disposal problems and/or to a more involved certification process. Excessively low inertia of a system, in particular for certain instances of application, is also not necessarily user friendly, in particular because low inertia can produce the feeling of reduced movement stability.

WO 2006/091494 A1 describes a surgical apparatus having a surgical device. Furthermore, the document discloses that a haptic device can be operated with what is known as admittance regulation or impedance regulation, the surgical device being mounted on these haptic devices. This surgical device can be a microscope, for example.

DE 10 2004 063 606 A1 describes a retaining apparatus, in particular for a medical optical instrument, having at least one rotary joint and having means for compensating for a load torque that the medical optical instrument creates at the rotary joint, wherein the means for compensating for the load torque comprise an electric motor.

US 2014/0229006 A1 describes a method for controlling a robot. It states that redundancy for positions of the joints of a robot is eliminated during path planning by inertia dependent selection of the positions of the joints.

SUMMARY

A technical problem that arises is that of providing a method for operating a surgical microscopy system and a surgical microscopy system that increase user friendliness and/or safety of operation during operation.

The solution to the technical problem is provided by a method for operating a microscopy system and a microscopy system as described herein.

The surgical microscopy system includes a microscope and a stand for supporting the microscope.

The stand includes at least one drive device or actuator configured to move the microscope. At least one control device is provided and configured to control an operation of the microscopy system. Specifically, the at least one control device is configured to determine a specified value or a specified change of a modulable inertia of the microscopy system based on at least one of: a state variable, user information, a force acting on the microscopy system, and a current instance of application. The at least one drive device is controllable such that a divergence between the specified value and an actual value of the modulable inertia is reduced or the modulable inertia is varied in accordance with the specified change.

The method for operating the microscopy system includes determining a specified value or a specified change of a modulable inertia of the microscopy system based on at least one of: a state variable of the microscopy system, user information, a force acting on the microscopy system, and a current instance of application. In addition, the method includes controlling the at least one drive device such that a divergence between the specified value and an actual value of the modulable inertia is reduced or the modulable inertia is varied in accordance with the specified change.

BRIEF DESCRIPTION OF THE DRAWINGS

The disclosure will now be described with reference to the drawings wherein:

FIG. 1 shows a schematic flowchart of a method according to a first exemplary embodiment of the disclosure, FIG. 2 shows a schematic flowchart of a method according to further exemplary embodiment of the disclosure, FIG. 3 shows a schematic flowchart of a method according to a further exemplary embodiment of the disclosure.

DESCRIPTION OF EXEMPLARY EMBODIMENTS

Figure 4:
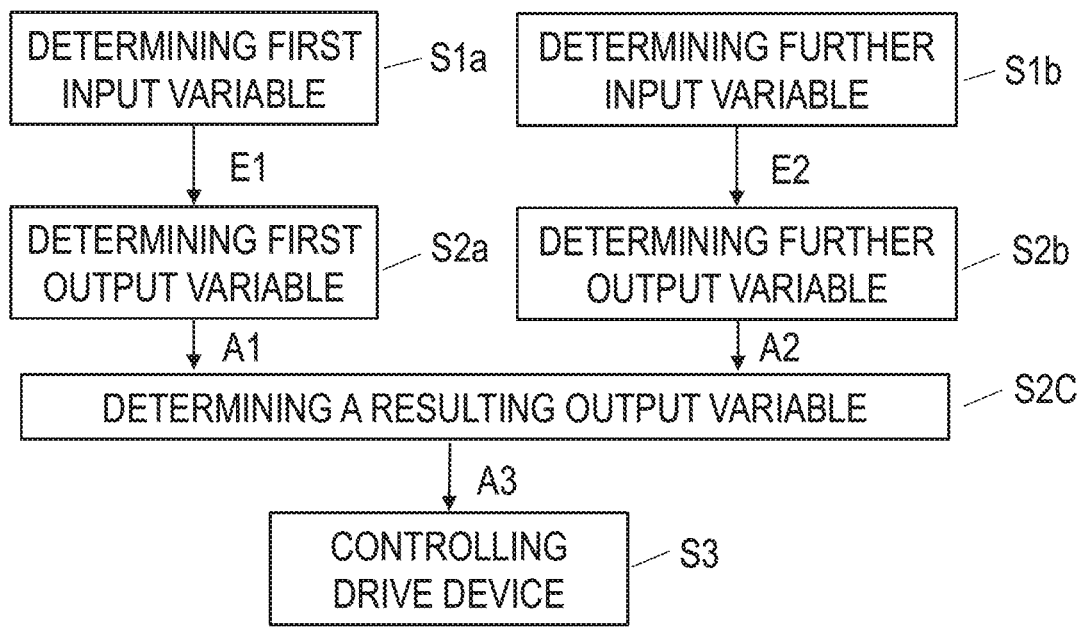
FIG. 4 shows a schematic flowchart of a method according to a further exemplary embodiment of the disclosure.

Identical reference signs hereinafter denote elements having identical or similar technical features.

For the purposes of this disclosure, a microscope refers to a device for magnified visual presentation of an examination object. The microscope can be a conventional optical microscope, which produces an enlarged image by making use of optical effects, in particular using means for beam guidance and/or beam shaping and/or beam deflection, for example lenses. However, the microscope can also be a digital microscope, wherein the image to be visualized by the microscope can be produced with an image capture device and can be displayed on an appropriate display device, for example a display.

The microscope can in particular include at least one eyepiece. The eyepiece refers to a part of the microscope through which or into which a user looks in order to view the image produced by the microscope. Moreover, the microscope includes at least one objective. This objective can produce a real optical image of an examination object. The objective in this instance can include optical elements for beam guidance and/or beam shaping and/or beam deflection.

The microscopy system moreover includes a stand for supporting the microscope. The microscope, in particular the microscope body, is arranged or arrangeable, in particular mountable, on the stand. It is possible that the microscope is mounted on a free end of the stand, in particular in mobile fashion, e.g., in pivotable fashion. The stand in this instance is configured in such a way that it permits movement of the microscope in the (work)space, in particular with at least one degree of freedom, typically with six degrees of freedom. It is of course also possible that the stand is configured in such a way that it permits movement of the microscope in space with a restricted number of degrees of freedom, that is to say in particular with fewer than six degrees of freedom.

A degree of freedom in this instance can be a degree of translational or rotational freedom. In particular, movement with three different degrees of translational freedom and three different degrees of rotational freedom can be permitted by the stand.

The stand can have or form one or more joints, in particular at least one rotary joint and/or at least one translational joint. The stand can also be configured in such a way that it permits movement of the microscope about/along each of the joints, each joint, e.g., permitting movement with a degree of rotational or translational freedom. Furthermore, the stand can have a base, the base being able to be arranged at a fixed location during operation of the microscopy system when used as intended.

The degrees of freedom in this instance can relate to a reference coordinate system. A vertical axis (z axis) of this reference coordinate system can be oriented parallel to gravitational force and counter thereto. An origin of this reference coordinate system can be, e.g., at a point of intersection between an axis of rotation of a first rotary joint of the stand and a floor area, the base of the stand being arranged on the floor area.

A longitudinal axis (x axis) of the reference coordinate system and a transverse axis (y axis) of the reference coordinate system can define a plane oriented perpendicularly with respect to the vertical axis. This plane can be, e.g., parallel to a floor area on which the microscopy system stands. Moreover, the longitudinal axis and the transverse axis can also be oriented orthogonally with respect to each other. Furthermore, it is possible that the axis of rotation of a rotary joint, in particular of a first rotary joint in a succession of joints of the stand, is oriented parallel to the vertical axis.

However, a reference coordinate system can also be a coordinate system that is fixed with respect to the microscope. In this case, a vertical axis (z axis) of this reference coordinate system can be oriented parallel to the optical axis of the microscope and away from the microscope. An origin of this reference coordinate system can be at the point of intersection between the optical axis and the objective.

As a further alternative, a reference coordinate system can also be a coordinate system that is fixed with respect to a focal point. In this case, a vertical axis (z axis) of this reference coordinate system can be oriented parallel to the optical axis of the microscope and away from the microscope. An origin of this reference coordinate system can be at the focal point.

The reference coordinate system can, in particular, be a Cartesian, right-hand coordinate system.

As a further alternative, the reference coordinate system can be a coordinate system that is fixed with respect to a base or a coordinate system that is fixed with respect to an operating element. An operating element allows a user to operate the microscopy system, in particular to actuate it for the purpose of positioning. An operating element can be a handle or a mouth switch, for example.

Moreover, the stand includes at least one drive device for moving the microscope. The stand typically includes multiple drive devices. A drive device in this instance refers to a device for producing a driving force or a drive moment. Such a drive device can be a servo motor, for example. Of course, the stand can also include means for transmitting forces or moments, e.g., gear units. In particular, it is possible for the at least one drive device to be actuated in such a way that the microscope executes a desired movement and thus a desired change of bearing in space or adopts a desired bearing in space. In this instance, a bearing refers to a position and/or an orientation. It is possible that a speed of the movement in the reference coordinate system and/or in a joint-specific coordinate system is restricted to a predetermined maximum speed in this instance. It is moreover possible that a size of the workspace of the stand is restricted.

The stand can include at least one joint having at least two parts that are mobile relative to one another. The drive device can be a drive device assigned to the joint. The drive device can be configured to drive at least one of the parts of the joint that are mobile relative to one another or to adjust the relative bearing of the two parts that are mobile relative to one another.

For example, the at least one drive device can be actuated in such a way that an optical axis of the objective adopts a desired orientation. Moreover, the at least one drive device can be actuated in such a way that a reference point of the microscope, e.g., a focal point, is positioned at a desired position in space.

A specified bearing in this instance can be prescribed by a user or by another superordinate system. Methods for controlling the at least one drive device on the basis of a specified bearing, an actual bearing and the kinematic structure of the stand are known to a person skilled in the art in this instance. The user in this instance can refer to a person who operates the microscope, in particular who looks into/through the eyepiece in order to obtain a magnified view of the object. It is possible that the microscope is what is known as a surgical microscope. In this case, the user can be a surgeon, in particular.

According to an aspect of the disclosure, a specified value or a specified change of a modulable inertia of the microscopy system is determined on the basis of a state variable of the microscopy system, in particular on the basis of the absolute value and/or direction thereof.

A state variable can be, e.g., a selected specified or actual value of a movement variable, a selected specified or actual value of an optical variable or a further variable that characterizes or represents a specified or actual operating state of the microscopy system. An optical variable can be a selected magnification of the microscope, a selected focal distance of the microscope or a further optical variable.

The modulable inertia in this instance refers to the inertia that the user senses when the microscopy system, in particular the microscope, is accelerated by the user, this inertia being adjustable as a result of operation of the at least one drive device. An inertia modulated by actuation of the at least one drive device correlates with or results in a force that the user needs to apply in order to accelerate the microscopy system in a desired manner when the at least one drive device is actuated at the same time and produces a corresponding moment.

The modulable inertia can be different than an effective inertia of the microscopy system in this instance, the effective inertia referring to an inertia that the user senses or feels when the microscopy system, in particular the microscope, is accelerated by the user when the at least one drive device is not actuated, that is to say does not produce a moment/force. In particular, this effective inertia can be dependent on, in particular proportional to, the ratio of force and acceleration in this case, the force needing to be applied by the user in order to accelerate the microscopy system in the desired manner. The sensed/effective inertia can—as illustrated in even more detail below—be dependent on a bearing/an position of the microscopy system in space and a direction of the exerted force, and conditional upon the kinematic structure of the microscopy system. It is possible that the direction of the force and the direction of the resulting acceleration are identical. Depending on the kinematic structure and position of the microscopy system, the direction of the force can also be different than the direction of the resulting acceleration, however.

The effective inertia can, in particular, be part of a mechanical impedance or a mechanical admittance of the surgical microscopy system, the mechanical admittance describing the ratio between applied force and resulting speed and the mechanical impedance describing the ratio between a selected speed and force resulting therefrom. In particular, the mechanical impedance describes that a movement of the microscopy system results in a force.

The modulable inertia in this instance must furthermore be distinguished from the real inertia of the microscopy system, the real inertia referring to the actual physical inertia of the microscopy system. In contrast to the effective inertia, this is not necessarily sensed by a user and is not variable by operation of the at least one drive device. Of course, the effective inertia is dependent on the real inertia, however.

It is admittedly possible that the modulable inertia is set to the value of the real inertia or the value of the felt/effective inertia of the microscopy system. The modulable inertia can also be set to different values, however. This can be achieved in particular if the at least one drive device is operated such that the force needing to be applied by the user in order to accelerate the microscopy system is reduced or increased. This is illustrated in even more detail below.

Within the realm of this disclosure, a force also refers to a torque, in particular about a predetermined axis.

A movement variable in this instance refers to a variable that describes the movement of the microscopy system, in particular the microscope. A movement variable can, in particular, refer to a jerk (a derivative of the acceleration), an acceleration, a speed or a path or spatial bearing. A movement variable for the purposes of this disclosure can also be a bearing of the microscopy system or a relative bearing between two parts of the microscopy system that are mobile relative to one another. Furthermore, a movement variable can be referenced to a translational movement or a rotational movement.

An effective inertia, a modulable inertia, a state variable, in particular a movement variable, a force, a specified value or a specified change can be directional variables, a directional variable being able to be determined as a function value of a function that is dependent on the direction. These directional variables and other directional variables can be referenced to a coordinate system in this instance, in particular to the reference coordinate system illustrated above.

However, these directional variables can also reference a coordinate system that is different than the reference coordinate system, for example one of the coordinate systems illustrated above, e.g., the coordinate system fixed with respect to the microscope, a coordinate system fixed with respect to a focal point, a coordinate system fixed with respect to an operating element or a coordinate system fixed with respect to a stand joint.

Furthermore, these variables, in particular the effective or modulable inertia, can relate to a reference point, in particular of the microscopy system. A reference point of the microscopy system can be for example an interaction point, a focal point, a center of gravity or a geometric center of the microscopy system, of a part of the microscopy system or of a part added to the microscopy system, for example of the microscope or of a mobile part of the stand. The reference point can also be a point on an axis of the coordinate system or a point of intersection of multiple axes of the coordinate system. The reference point can also be a point on an axis of the stand.

An interaction point can, in particular, be a point, for example a center, of a section or operating element that is operated for a user interaction, in particular operation of the surgical microscopy system by the user, during operation as intended.

Furthermore, these variables, in particular the effective or modulable inertia, can relate to a reference axis, in particular of the microscopy system. In particular, the effective inertia or modulable inertia relating to the reference axis can permit determination of a moment of inertia for a rotation about this reference axis. A reference axis of the microscopy system can be an axis of the coordinate system. The reference axis can also be an axis of the stand.

It is possible that a movement variable is determined on the basis of one or more further movement variable(s) or the time characteristic thereof, for example the spatial position of the microscopy system or a relative position of joints of the microscopy system that are movable relative to one another or a trajectory of the microscopy system.

Alternatively or cumulatively, the specified value or the specified change of the modulable inertia is determined on the basis of user information. As illustrated in even more detail below, user information can be in particular a user interaction modality, a user property or a user specific operating parameter set.

As a further alternative or cumulation, the specified value or the specified change can be determined on the basis of a force acting on the microscopy system, in particular on the basis of the absolute value and/or direction of said force. This acting force can, in particular, be the (weight) force resulting from a load of the microscopy system. Alternatively or cumulatively, the force acting on the microscopy system can be a force applied by the user. A further movement variable can be the direction of the variables illustrated above.

As such, it is for example possible to choose the specified value or the specified change such that the modulable inertia referenced to the direction of the force applied by the user is decreased, in particular to a predetermined minimum value. Furthermore, the specified value or the specified change can be chosen such that the inertia referenced to other directions is increased. This advantageously results in the direction of force and the direction of the resulting acceleration being as identical as possible, allowing convenient and intuitive handling of the microscopy system. In particular, it is therefore possible to reduce the effect that the direction of force and the direction of acceleration differ, which—as illustrated above—can be conditional upon a kinematic structure and/or a spatial bearing of the microscopy system.

It is also possible to choose the specified value or the specified change such that the modulable inertia referenced to current actual direction of movement is decreased, in particular to the predetermined minimum value. Furthermore, the specified value or the specified change can be chosen such that the inertia referenced to other directions is increased. This advantageously results in a further acceleration in the actual direction of movement being simplified for the user, whereas accelerations in other directions can be hampered.

This advantageously results in the direction of force and the direction of the resulting acceleration being as identical as possible, allowing convenient and intuitive handling of the microscopy system.

Alternatively or cumulatively, the specified value or the specified change of the modulable inertia is determined on the basis of a current instance of application. A current instance of application can be a surgical phase, for example. A surgical phase can be a preoperative phase, an intraoperative phase or a post-operative phase. As an example, and not conclusively, a surgical phase can be a resection phase, a suturing phase or a clipping phase.

A current instance of application can be determined or identified on the basis of at least one piece of input information in this instance, e.g., with a method for plan or pattern recognition known to a person skilled in the art, exemplary methods being illustrated in even more detail below. Input information can be a state variable of the microscopy system, in particular of the microscope, for example.

Input information can also be input by a user, e.g., with an appropriate input device. As such, a user can select a current instance of application using an appropriate input, for example.

As illustrated in even more detail below, a current instance of application can also be a movement phase.

One of the aforementioned state variables, one of the aforementioned pieces of user information and/or one of the aforementioned forces acting on the microscopy system can also be referred to in this instance as an input variable for a method for determining the specified change or the specified value. The specified value or the specified change can also be referred to as an output variable for this method.

The output variable in this instance can be determined on the basis of precisely one input variable or a set comprising multiple input variables.

A relationship between the output variable and the at least one input variable can be a functional relationship. Furthermore, there can be a relationship in the form of a, in particular parameterizable, characteristic curve. It may also be possible that respective specific output variables are determined for different input variables or sets of input variables, a resulting output variable then being determined on the basis of all of these specific output variables, for example by fusion, superposition, summation, product formation or averaging, in particular arithmetic or geometric averaging, product formation or averaging, in particular arithmetic or geometric averaging.

A method for determining the output variable on the basis of at least one input variable can also be a fuzzy logic method known to a person skilled in the art. This allows in particular fuzzy expert knowledge to be modelled algorithmically.

Such a method can also be a pattern recognition method, for example a method using neural networks, an SVM (support vector machine) based method or a method using ensemble methods. Methods using data mining methods, in particular using data stream mining methods, are also suitable for determining the output variable, in particular at runtime.

A method for determining the output variable can also be a Markov decision process-based method. This advantageously allows the human decision processes to be modelled with good accuracy. Reinforcement learning methods that allow a model to be generated for a Markov decision process-based method automatically are also usable.

The system for determining the output variable can also be what is known as a behavior-based system. Such a system, in particular the control and evaluation device thereof, can use a predetermined behavior repertoire, which is used to determine what behavior is selected at what time. In the present case, the repertoire can be used to determine what output variable needs to be selected at what time. This repertoire can be dynamically variable, in particular extendable, e.g., at runtime. This can be accomplished by using learning methods known to a person skilled in the art. In particular, it may be possible that the learning method involves past experiences being combined with the behavior stipulated in the predetermined repertoire.

Furthermore, the method for determining the output variable can be a self-learning method. The microscopy system can therefore be in the form of a self-learning system. The learning process in this instance can be performed before use of the microscopy system, e.g., during calibration in the laboratory, or at runtime. By way of example, evolutionary algorithms or the aforementioned reinforcement learning methods can be used as part of optimization methods. Measurements, in particular cost functions, for optimization can in this instance be time dependent measurements, trajectory dependent measurements or measurements describing a quality of movement. Furthermore, output signals from sensors external or internal to the microscopy system can be used in order to optimize determination of the output variable, for example sensors for recording forces that the user applies when operating the microscopy system.

In this instance, a specified change can be used to stipulate in particular whether the modulable inertia is supposed to be increased or decreased. Furthermore, the specified change can also be used to stipulate an absolute value of the increase or decrease. However, this is not mandatory. As such, it is for example possible that the specified change is used to stipulate only an increase or decrease, but not an absolute value of this specified change.

Furthermore, the specified change can be used to stipulate a rate of change, that is to say an absolute value of the change per predetermined time interval. As such, it is for example possible that the specified change is used to stipulate an increase or decrease and a rate of change, but not an absolute value of the specified change.

In other words, the at least one state variable, the user information, the current instance of application and/or the force acting on the microscopy system can be taken as a basis for stipulating whether the modulable inertia is increased or decreased. Furthermore, it is possible, but not mandatory, for the rate of change to be stipulated. Furthermore, it is possible, but likewise not mandatory, for the absolute value of the change to be stipulated.

An input variable can be determined in this instance. For the purposes of this disclosure, the term "determine" also refers to capture. By way of example, the applicable variable can be captured with at least one appropriate capture device, e.g., a sensor. However, the term "determine" also covers determination of a variable by computation, for example with model-based calculation. The term "determine" can also refer to determination with suitable methods, e.g., estimation, identification or prediction methods. Such determination can also be effected on the basis of at least one captured variable.

Furthermore, the at least one drive device is controlled such that a divergence between the specified value and an actual value of the modulable inertia is reduced. This can be accomplished by determining the actual value of the modulable inertia, which is illustrated in even more detail below. Alternatively, the at least one drive device can be controlled such that the modulable inertia is varied in accordance with the specified change.

In other words, the modulable inertia can be set to a desired specified value or varied in a desired manner. This adjustment can be used to vary the modulable inertia of the microscopy system, in particular from an output value (actual value of the modulable inertia) to the specified value. For the purposes of this disclosure, a variation in the modulable inertia can thus take place as a result of determination of the specified value or the specified change and corresponding control of the at least one drive device.

The specified value in this instance can be determined during operation of the microscopy system, in particular during a movement of the microscopy system performed by the user. It is, e.g., possible that the specified value is determined or adapted dynamically or continuously. Accordingly, the modulable inertia can also be changed during operation of the microscopy system, in particular during the movement performed by the user. In particular, this variation can take place at the beginning of the movement.

It is possible that a surgical microscopy system includes at least one control and evaluation device, the specified value or the specified change being determinable with the control and evaluation device. Furthermore, the actual value of the modulable inertia can be determinable with the control and evaluation device. Furthermore, the at least one drive device can be controlled with the control and evaluation device.

The control and evaluation device in this instance can be in the form of a computing device or can include at least one computing device. Such a computing device can, in particular, be in the form of a microcontroller or in the form of an integrated circuit, for example in the form of an field-programmable gate array (FPGA).

It is, e.g., possible that the specified value of the modulable inertia is set to a predetermined minimum value. The predetermined minimum value can be a value close to zero in this instance. This means that the user only needs to apply as little force as possible in order to overcome the inertia when moving the microscopy system. In this case, e.g., the at least one drive device can produce the forces needed to overcome the inertia, such that the user detects almost no forces required to overcome the inertia during operation, in particular acceleration. This can also be referred to as inertia compensation. The predetermined minimum value can be chosen, e.g., such that the force needing to be applied by the user to overcome the inertia is not higher than a predetermined maximum value.

However, this inertia compensation is only one possible application scenario. In other application scenarios, in particular incomplete compensation for the inertia can be desirable, e.g., a targeted decrease. Alternatively, however, a targeted increase in the inertia may also be desired.

It is, e.g., possible that the specified value of the modulable inertia can be taken as a basis for determining a specified inertial force, this specified inertial force referring to a force that the user is supposed to apply in order to accelerate the microscopy system, in particular in order to accelerate with a desired amplitude and direction.

The at least one drive device can then be controlled such that a divergence between this specified inertial force and an actual inertial force of the user operation is reduced, the actual inertial force referring to the force that a user currently applies in order to accelerate the microscopy system.

It is, e.g., conceivable that the actual inertial force is determined on the basis of an actual value of the modulable inertia, this actual inertial force referring to a force that the user needs to apply in order to accelerate the microscopy system, in particular in order to accelerate with a desired amplitude and direction, in the actual state. The actual value of the modulable inertia (and hence also the actual inertial force) can be determined in model-based fashion in this instance. This is illustrated in even more detail below. In particular, the actual value determined for the modulable inertia can also be the actual value of the effective inertia.

Of course, the actual inertial force can also be determined in another manner, however, e.g., on the basis of an actual movement variable, in particular in sensor assisted fashion.

This advantageously results in usability when moving or accelerating the microscopy system being increased, since the reduction or change can, in certain instances of application, reduce an effort for the user for moving the microscopy system or can assist the user in performing a desired movement/a desired task.

In particular, the illustrated assistance permits more efficient use of the microscopy system, since movement of the microscopy system to a target position in a faster time is also permitted. The subjectively perceived usability when operating the microscopy system is also increased.

It is also possible, in further instances of application, to prevent or hamper an undesirable movement by varying or adjusting the modulable inertia. It is therefore also advantageously possible for safety of operation when operating the microscopy system to be increased.

In particular, it is advantageously possible for the modulable inertia to be varied during the movement of the microscopy system by the user. It is thus, e.g., conceivable to take at least one state variable, to take user information and/or to take a force acting on the microscopy system as a basis for determining a current instance of application, e.g., a use scenario, a surgical phase or a movement phase of the microscopy system, with the specified value or the specified change then being set on the basis of the instance of application.

In contrast to the impedance regulation and admittance regulation illustrated at the outset, the specified value or the specified change of the modulable inertia is not predetermined, however, but rather is obtained in particular on the basis of a state variable, user information and/or a force acting on the microscopy system and/or a current instance of application, in particular at runtime.

In an exemplary embodiment, the specified value or the specified change is determined on the basis of the acceleration of the microscopy system. For the purposes of this disclosure, accelerating refers both to accelerating to achieve higher speeds and to accelerating to achieve lower speeds (decelerating). A positive acceleration can also refer to an acceleration that is at least proportionally oriented in the direction of an actual speed of the movement of the microscopy system. In this instance, such a proportion can be higher than 50%, in particular. Accordingly, a negative acceleration can refer to an acceleration that is at least proportionally oriented counter to the direction of an actual speed of the movement of the microscopy system. In this instance, such a proportion can be higher than 50%, in particular.

The acceleration in this instance can be different than an acceleration brought about by gravitational force.

As illustrated above, the acceleration can be captured or determined. In particular, the acceleration can be determined on the basis of an acceleration or a change in the speed of a drive shaft of the at least one drive device illustrated above. Furthermore, the acceleration can be taken as a basis for determining a movement phase of the microscopy system. This is illustrated in even more detail below.

Alternatively or cumulatively, the specified value or the specified change can be determined on the basis of the speed of movement of the microscopy system.

As such, it is, e.g., possible that a positive acceleration or a positive acceleration whose absolute value is higher than a predetermined threshold value results in the specified value of the modulable inertia being reduced, in particular in a predetermined manner, in particular by a predetermined absolute value and/or at a predetermined rate of change or by an absolute value and/or at a rate of change that is dependent on the acceleration and/or at least one other of the aforementioned input variables.

As such, the inertia can be, e.g., reduced if the acceleration is positive or positive and higher than a predetermined threshold value. It is also conceivable that, in such a case, the inertia is reduced only if a speed of the microscopy system is zero or lower than a predetermined threshold value. In this case, a phase of positive acceleration can be identified. This advantageously allows fast and simple acceleration of the microscopy system by the user to be made possible, with in particular an effort for this acceleration being reduced. It is also conceivable that, in such a case, the inertia is not reduced or is even increased if a speed of the microscopy system is higher than the/a predetermined threshold value or identical to this threshold value. This hampers further acceleration at high speeds.

Furthermore, the inertia can be, e.g., reduced if the acceleration is negative or negative and lower than a predetermined threshold value. It is also conceivable that, in such a case, the inertia is reduced only if a speed of the microscopy system is different than zero or higher than a predetermined threshold value. In particular, a deceleration phase, that is to say a phase of negative acceleration, can be identified in this case, the deceleration phase being taken as a basis for reducing the modulable inertia. This advantageously allows fast and simple deceleration of the microscopy system by the user to be made possible, with in particular an effort for this deceleration being reduced.

The inertia can also be, e.g., reduced if the acceleration is zero or lower than a predetermined threshold value and the speed of movement is larger than zero or higher than a predetermined threshold value. In this case, a phase of continuous movement can be identified, and operation by the user can be assisted by the reduction.

It is also conceivable to increase the modulable inertia if the acceleration is higher than a maximum permissible threshold value. This advantageously results in increased safety of operation, since the associated increased effort hampers further acceleration and hence a potentially undesirably high speed.

The modulable inertia can also be increased if the number of changes of a direction of the acceleration within a predetermined period is larger than a predetermined threshold number to more than a predetermined extent.

Alternatively or cumulatively, the inertia can be increased if the number of changes of a direction of the force acting on the microscopy system within a predetermined period is larger than a predetermined threshold number to more than a predetermined extent. Both advantageously allow tremor dependent determination of the specified change or of the specified value of the modulable inertia, in particular reduction of effects of a tremor by the user during operation of the microscopy system. It is thus possible, by way of example, for a tremor to be detected if the illustrated number is larger than the aforementioned threshold number.

As a further alternative or cumulation, the inertia can be increased if a tremor is detected on a frequency basis. This can involve, e.g., a frequency content of a change of direction, of a change of force, of a change of acceleration, of a change of speed or of a change of position being determined, with a tremor being detected if a frequency based criterion is satisfied, for example if a level of the spectrum at predetermined frequencies is higher than a predetermined threshold value.

It is also conceivable that, in such a case, the inertia is increased only if additionally, a speed of the microscopy system is zero or lower than a predetermined (low) threshold value. Of course, it is also conceivable to detect a tremor by a user in another manner.

This makes it possible to prevent the tremor by the user from resulting in an undesirable change of bearing of the microscope, which could also lead to an undesirable variation in the image detail presented by the microscope. This is easily possible in particular at large working intervals and magnifications, since small changes of position can then lead to comparatively large variations in the image detail.

In a further exemplary embodiment, it is possible that the modulable inertia is increased if the speed of the microscopy system is higher than a predetermined speed threshold value, in particular in the event of a further positive acceleration. It is furthermore possible that the change of the modulable inertia in this case is proportional to the divergence between the speed and the illustrated predetermined threshold value. In other words, the inertia can be increased more and more as the speed increases. This advantageously results in an increase in the speed being hampered by the ever-increasing inertia required and the associated force for acceleration, which increases the safety of operation of the microscopy system.

Furthermore, the modulable inertia can be decreased if the speed of the microscopy system is higher than a predetermined speed threshold value and a negative acceleration, that is to say a deceleration, occurs.

It is also conceivable to increase or decrease the modulable inertia accordingly if the speed is lower than a further (lower) threshold value.

In a further exemplary embodiment, it is possible to reduce the modulable inertia as the speed increases, in particular if the speed is lower than the speed threshold value illustrated above. As such, examinations have shown that the inertia sensed by a human user is speed dependent, in particular that a mass sensed by the user also increases as speed increases. The described reduction of the modulable inertia in the event of a speed increase allows this sensation to be compensated for at least in part. This means that the speed dependent sensation of a change of the modulable inertia is reduced or eliminated by the determination of the specified value or the specified change.

In certain instances of application, it may be desirable not to set the modulable inertia too high, in particular so as not to allow the forces required for a movement to become too large. This can mean that the modulable inertia is not set to a value that is higher than a predetermined maximum value. On the whole, it is desirable to find a trade-off between a high modulable inertia to improve user friendliness and a modulable inertia that is chosen to be too high. This trade-off can be ascertained empirically.

Furthermore, it is possible to increase the modulable inertia if a jerk or an absolute value of the jerk is higher than a predetermined threshold value. This advantageously achieves gentler acceleration and reduces vibrations induced by the jerk (jolt). Furthermore, it advantageously results in a large and in particular sudden burst of force by a user being converted into a small jolt. This in turn advantageously increases user friendliness.

Furthermore, the specified value or the specified change can be determined on the basis of a current spatial bearing. If the current spatial bearing corresponds to a predetermined target bearing or if the current spatial bearing is in a predetermined target region, for example, then the modulable inertia can be increased. The target bearing or region can be predetermined, for example by a user input, for example by an audible user input, for example by a voice command, or by a haptic user input, for example by operation of an appropriate user interface. It is also possible for the target region to be determined during the runtime, for example on the basis of the state variables, in particular movement variables. If for example it is detected that the microscopy system is in one bearing for longer than a predetermined period, in particular at a time after a change of bearing to more than a predetermined extent, or that a bearing of the microscopy system does not change to more than a predetermined extent, then the bearing can be determined as the target bearing and/or a region of predetermined size around the bearing can be determined as the target region.

However, it is also possible that the modulable inertia is varied such that the modulable inertia is independent of bearing. As such, depending on the kinematic structure of the microscopy system or of the stand, different effective inertias exist in different positions of the microscopy system, which means that changes of bearing can also cause changes in the effective and hence also modulable inertia. By setting an inertia that is independent of bearing, it is advantageously possible to reduce or eliminate the effects of a position dependent effective inertia on operation by the user.

Furthermore, the specified value or the specified change can be determined such that the modulable inertia is independent of direction. On the basis of the kinematic structure illustrated above, an effective inertia is likewise direction specific. This can mean in particular that different levels of force are needed to accelerate the microscopy system in different directions, but with the same absolute value. This directional dependency of the inertia can in turn be dependent on the position of the microscopy system. By setting an inertia that is independent of direction, it is advantageously possible to reduce or eliminate the effects of a direction dependent effective inertia of this kind on operation by the user.

Furthermore, it is possible to determine the specified value or the specified change on the basis of a direction of movement, that is to say in a manner specific to the direction of movement. As a result, it is advantageously possible for the microscope arranged on the stand to appear to be decoupled from the stand and to be moved with a predetermined defined inertia in space.

Furthermore, it is conceivable to determine the specified value or the specified change on the basis of the degree of freedom of movement, that is to say in a manner specific to the degree of freedom of movement. It is therefore possible for modulable inertias to be set independently of, in particular differently than, one another for movements about and/or along different degrees of freedom of movement. This allows, e.g., a modulable inertia for a rotational/translational movement about/along a first axis/direction to be set such that it is different than the modulable inertia for a movement about/along an axis/direction that is different than the first axis/direction or such that these modulable inertias are identical.

As such, it is possible to set a modulable inertia for a movement with one or more (but not all) degrees of freedom to be smaller to a predetermined extent than the modulable inertia for a movement with the remaining degrees of freedom. This allows in particular movements with these degrees of freedom to be promoted, while the system acts comparatively more sluggishly for the user in the event of a movement with the remaining degrees of freedom. In particular, a modulable inertia for a movement along or parallel to an optical axis of the microscope can be set to be smaller than the modulable inertia for movement along other spatial directions.

The specified value or the specified change can also be determined such that the modulable inertia is increased if the bearing, in particular the position, of the microscopy system diverges from an edge of a workspace to no more than a predetermined extent. The workspace can be a predetermined workspace, in particular a workspace predetermined by the user, and, e.g., can correspond to a subrange of the maximum available workspace of the microscopy system. However, the workspace can also correspond to the maximum available workspace of the microscopy system. Alternatively or cumulatively, the modulable inertia can be increased for movements that further decrease the distance from the edge of the workspace.

If redundant options exist for performing a movement, for example redundant movement profiles about/along the axes of the microscopy system, then the modulable inertia can be set to different values for different instances of these movement profiles. This allows a movement in accordance with one of the movement profiles to be selectively hampered or simplified for the user in comparison with the other movement profiles.

It is also possible to determine a position of a drive shaft of a drive device, the specified value or the specified change being determined such that the modulable inertia is increased if the position diverges from the position of an end stop of the drive device, or the position stipulated by an end stop of the stand joint driven by the drive device, to no more than a predetermined extent. Alternatively or cumulatively, it is also possible in this case to increase the inertia only for movements of the drive device, in particular of the drive shaft, that decrease this distance further.

Alternatively or cumulatively, it is possible to increase the inertia in this case if the microscopy system is accelerated in the direction of the edge of the workspace or in the direction of the end stop. Alternatively or cumulatively, it is possible to decrease the modulable inertia if the microscopy system is accelerated, that is to say in particular decelerated, away from the edge region or away from the end stop.

This advantageously reduces wear on the microscopy system as a result of mechanical contact with the end stops.

In summary, it is thus possible to identify an instance of application on the basis of one or more state variables, in particular movement variables, in which case the specified value or the specified change is determined in a manner specific to the instance of application.

This advantageously results in increased user friendliness, since different modulable inertias are selectable for the different demands of the different instances of application and therefore always provide optimum assistance for the user during operation of the microscopy system. Similarly, as illustrated above, an improvement in the safety of operation or fail-safety can be obtained.

In a further exemplary embodiment, a manipulability or a variation in the manipulability is determined. The manipulability in this instance refers to a measure of the ability of the microscopy system to react to a force in a bearing. The manipulability can be direction dependent, that is to say dependent on the direction of this force. The manipulability is therefore dependent on bearing and direction. There are various metrics to describe the manipulability, these being described in the book by Bruno Siciliano and Oussame Khatib, "Springer Handbook of Robotics", Springer-Verlag, Berlin, Heidelberg, 2007, for example.

The modulable inertia can be higher when manipulabilities are low than when manipulabilities are comparatively high. What is known as a singularity exists when the manipulability in a bearing is zero for one or more direction (s) of force. In this case, the microscopy system cannot react to such a force. Such singularities, but also bearings with low manipulabilities, are normally undesirable.

Furthermore, the specified value or the specified change is determined on the basis of the manipulability or the variation therein. By way of example, the specified value or the specified change can be determined such that an acceleration or a movement in the direction of a bearing with a manipulability that is lower than a predetermined threshold value results in the modulable inertia being increased. Alternatively or cumulatively, the specified value or the specified change can be determined such that an acceleration or a movement away from a bearing with a manipulability that is lower than a predetermined threshold value results in the modulable inertia being decreased.

It is also conceivable that, in such a case, the inertia is changed as illustrated only if the microscopy system is additionally in a bearing with a manipulability that is lower than the predetermined threshold value. This advantageously allows movements into singularities or bearings with low manipulability to be hampered. Furthermore, it is advantageously possible for movements away from or out of singular bearings or bearings with low manipulability to be facilitated.

In particular, the modulable inertia can be adapted by the specified value or the specified change such that a user is not surprised by the occurrence of singularities or bearings with low manipulability.

On the whole, this advantageously results in increased user friendliness, since movement of the microscopy system into unfavorable bearings is hampered.

In a further exemplary embodiment, a specified direction of movement and an actual direction of movement are determined. The actual direction of movement in this instance can be determined on the basis of one or more of the illustrated input variables, in particular movement variables. E.g., it is possible to determine the actual direction of movement in model-based fashion. By way of example, a force applied to the microscopy system by the user can be determined, in which case an actual direction of movement is determined in model-based fashion. Of course, the direction of movement can also be determined in another manner, e.g., by an external bearing detection system. The actual direction of movement can also be one of the directions of movement illustrated above.

A specified direction of movement can be predetermined or determined at runtime, in particular on the basis of at least one input variable, e.g., a force applied by the user or the direction of said force. By way of example, the specified direction of movement can correspond to this direction of force.

The specified direction of movement can be determined, e.g., by suitable methods for estimating/predicting the direction of movement, for example likewise on the basis of a time characteristic of movement variables. Specified directions of movement can also be prescribed by a user input.

Furthermore, the specified value or the specified change is determined on the basis of the divergence between the specified and actual directions of movement. By way of example, the specified value or the specified change can be determined such that the modulable inertia, in particular referenced to the actual direction of movement, is increased if the actual direction of movement diverges from the specified direction of movement to more than a predetermined extent. It is also possible for the specified value(s) or the specified change(s) to be determined such that the modulable inertia is increased for a movement component of the actual direction of movement whose direction is different than the specified direction of movement, e.g. is oriented perpendicularly with respect thereto.

In this instance, the increase in the modulable inertia can be, e.g., proportional to the divergence. It is also possible to determine the specified value or the specified change such that the modulable inertia, in particular referenced to the actual direction of movement, is decreased if the actual direction of movement diverges from the specified direction of movement to less than the predetermined extent or to the predetermined extent.

It is also possible to set the specified value or the specified change in a manner specific to the direction of movement such that the modulable inertia is higher for directions of movement that diverge from the specified direction of movement to more than a predetermined extent than for directions of movement that diverge from the specified direction of movement to less than the predetermined extent or to the predetermined extent.

This advantageously allows movement components that are undesirable to the user to be reduced or completely eliminated during operation. This in turn advantageously increases user friendliness.

In a further exemplary embodiment, a movement phase of a movement of the microscopy system is determined. The movement can be used in particular for positioning the microscopy system, in particular the microscope. Furthermore, the specified value or the specified change is determined on the basis of the movement phase.

A movement phase in this instance can refer to an instance of application. Various movement phases, that is to say for example a phase of positive acceleration, a phase of continuous movement or a deceleration phase, have been explained above. A sequence of these phases can be a coarse positioning phase, which likewise forms a movement phase. Another movement phase can be a fine positioning phase.

Coarse positioning in this instance refers to a normally fast movement into a target region with a low accuracy requirement for the positioning, wherein larger distances are covered in comparison with fine positioning and a target is unknown. Fine positioning in this instance refers to movement with high precision, at lower speed, normally performed over short distances in comparison with coarse positioning, wherein a comparison is frequently made between attainment of the target and the current position.

A coarse positioning phase and a fine positioning phase can be identified on the basis of a time characteristic of at least one state variable, in particular a movement variable, for example. A fine positioning phase can be identified when a speed is lower than a predetermined threshold value and a bearing of the microscopy system changes to no more than a predetermined extent, for example. When a positioning phase is identified, the modulable inertia can be increased. Different modulable inertias can be set in the various movement phases.

It has likewise been explained that the movement phase can be determined on the basis of at least one or more input variable(s), in particular a movement variable or a force acting on the microscopy system and in particular on the basis of the time characteristic of said force. Of course, other types of determination of the movement phase are also possible, however. A movement phase in this instance can be identified, e.g., by methods for plan detection or one of the methods for pattern recognition explained above. This advantageously results in user friendliness being increased, as likewise explained above.

In a further exemplary embodiment, the specified value or the specified change is additionally set on the basis of a duration of the movement phase. The duration can, in particular, be a forecast duration. Suitable forecast methods are known to a person skilled in the art. If for example it can be forecast that a phase of continuous movement is still present for at least a predetermined period, then the specified value or the specified change can be determined such that the modulable inertia is increased. This advantageously results in uniform movements being stabilized, in particular because accelerations that disrupt this uniform movement need to be countered by large inertial forces.

In a further exemplary embodiment, the specified value or the specified change is determined on the basis of at least one user property.

By way of example, a user property can be a user bearing, in particular relative to the microscopy system. It is known that a user can exert forces on the microscopy system to different degrees in different user bearings, e.g., different maximum forces in certain directions. Therefore, the specified value or the specified change can be determined such that the modulable inertia is adapted to the opportunities for force exertion. By way of example, the user bearing can be taken as a basis for determining a maximum force or a maximum directional force that the user can exert on the microscopy system, the modulable inertia then being changed such that this maximum force permits a predetermined acceleration of the microscopy system.

It is also possible for the user property determined to be an anatomical or physiological property, e.g., a height, of the user and for the specified value or the specified change to be determined on the basis of the anatomical or physiological height. The user property can, e.g., be captured or else ascertained in sensor assisted fashion. A user property may also be known beforehand, e.g., as a result of an input of the user property, for example in the form of a user profile.

Furthermore, the user property determined can be a user condition, for example a level of fatigue, a level of ability to concentrate, a level of exhaustion or another user condition. The specified value or the specified change can then be determined on the basis of the user condition. By way of example, a level of fatigue higher than a predetermined threshold value can result in the specified value or the specified change being determined such that the modulable inertia is increased. A similar effect can result from the level of ability to concentrate falling.

Furthermore, the specified value or the specified change can be determined on the basis of a selected operating parameter set. The operating parameter set can be a user specific operating parameter set. This can be provided/stipulated automatically or by user input. The parameter set can also be determined on the basis of user properties, for example on the basis of a height of the user or a maximum exertable force of the user. The operating parameter set in this instance can include at least one, but typically multiple, parameters representing the modulable inertia. Furthermore, the operating parameter set can also include further parameters for operating the microscopy system, for example a standard magnification, a standard lighting intensity or other operating parameters. An operating parameter in this instance can be a state variable.

Furthermore, the specified value or the specified change can be determined on the basis of a selected focus value. By way of example, different specified values or specified changes can be determined for different focus values.

Different sensitivities for the imaging by the microscope with respect to movements, in particular with respect to rotational movements about a focal point, are obtained for different focal planes. The adjustment of the specified value or specified change can then be used to set the modulable inertia to be higher for high sensitivities than for comparatively lower sensitivities. By way of example, the modulable inertia can be set to be higher the higher the focus value, that is to say the focal length. Typically, the modulable inertia in this instance is set on the basis of the focus value, as described, only in relation to rotational movements about the focal point. The modulable inertia referenced to translational movements in this instance cannot be varied on the basis of the focus value, that is to say cannot be identical for different focus values or all focus values.

The therefore increased modulable inertia advantageously results in the microscopy system and hence also the imaging becoming less sensitive toward undesirable movements.

Furthermore, the specified value or the specified change can be determined on the basis of a mode of user interaction. A mode of user interaction can be a haptic mode of interaction, for example. A haptic mode of interaction can be a two-handed mode of interaction or a single-handed mode of interaction, in particular. Another mode of interaction can be a mouth-controlled mode of interaction. This can advantageously achieve the effect that the modulable inertia is adapted to the different opportunities, in the different modes of interaction, for applying and sensing forces for operating the microscopy system. By way of example, a user can exert and sense different forces for operation when operating with both hands than when operating with mouth control.

Similarly, different modes of user interaction can have different associated movement spaces and patterns. It is therefore possible for a movement space or pattern to be determined on the basis of a mode of user interaction, the specified value or the specified change being able to be determined in a manner adapted to these, that is to say on the basis of these, movement spaces and patterns.

Alternatively or cumulatively, a movement pattern can be detected and the modulable inertia can be set in a manner specific to the movement pattern. If, e.g., an overshoot is detected during the movement of the microscopy system, then the specified value or the specified change of the modulable inertia can be determined such that the modulable inertia is increased further in a movement phase of negative acceleration. By way of example, an overshoot can be detected when the microscopy system moves into a bearing or a region, in particular a target bearing or a target region, then moves out of the bearing or the region and then moves into the bearing or the region again, in particular in a period of time that is lower than a predetermined threshold value. This can advantageously achieve the effect that deceleration is facilitated for a user, since the detected overshoot provides an indication that the user is unsuccessful in decelerating the microscopy system as desired.

Furthermore, the specified value or the specified change can also be determined on the basis of a divergence between a specified trajectory of the microscopy system and an actual trajectory of the microscopy system.

In accordance with the above explanations concerning the actual direction of movement, the actual trajectory can be determined on the basis of one or more of the illustrated input variables, in particular movement variables, in particular in model-based fashion. Of course, the actual trajectory can also be determined in another manner, e.g., by an external bearing detection system.

A specified direction of movement can be predetermined or determined at runtime, in particular on the basis of at least one input variable, e.g., a force applied by the user or the direction of said force.

The specified trajectory can also be determined by suitable methods for estimating/predicting the direction of movement, for example likewise on the basis of a time characteristic of movement variables. Specified directions of movement can also be prescribed by a user input.

Furthermore, the specified value or the specified change is determined on the basis of the divergence between the specified and actual trajectories. By way of example, the specified value or the specified change can be determined such that the modulable inertia is increased if the actual trajectory diverges from the specified trajectory to more than a predetermined extent. In this instance, the increase in the modulable inertia can be, e.g., proportional to the divergence. It is also possible to determine the specified value or the specified change such that the modulable inertia is decreased if the actual trajectory diverges from the specified trajectory to less than the predetermined extent or to the predetermined extent. It is also possible for the modulable inertia to be increased, in particular to a predetermined threshold value, for accelerations that cause a movement away from the specified trajectory. It is also possible for the modulable inertia to be decreased, in particular to a predetermined threshold value, for accelerations that cause a movement toward or along the specified trajectory.

This advantageously results in improved user friendliness, since the modulable inertia can be adapted to the user.

In a further exemplary embodiment, a load of the microscopy system is determined. The load in this instance can correspond to a weight. The load can be or can include a weight of the microscope arranged on the stand, for example. Alternatively or cumulatively, the load can also be determined by the weight of a further device arranged on the stand, for example a lighting device or image capture device, in particular for optical bearing capture. Furthermore, the specified value or the specified change is determined on the basis of the load.

The load can, in particular, be determined by methods (calibration methods) known to a person skilled in the art. A calibration method can be what is known as a balancing trip, for example.

In particular, the specified value or the specified change can be determined on the basis of the load such that an inertia resulting from the load is not part of the modulable inertia or is only a predetermined proportion of the modulable inertia. This advantageously results in a load independent or load compensated modulable inertia.

It is also possible to set the specified value or the specified change in such load specific fashion that the modulable inertia is load specific, in particular is different for different loads. In particular, the specified value or the specified change can be chosen for different loads such that a difference between the modulable inertia is larger than the difference between the effective inertias for these different loads. This advantageously allows the sensation of a load difference to be increased, which means that the user's attention can be drawn to an altered load situation. It is therefore also possible for the modulable inertia to be adapted to a user expectation, in particular, e.g., if the user expects a higher inertia than the effective inertia.

In a further exemplary embodiment, the microscopy system is movable about and/or along a first axis and about and/or along at least one further axis, wherein the specified value or the specified change is set in axis specific fashion. The axes can be axes of a coordinate system. Furthermore, axes can also be axes of joints of parts of the microscopy system that are movable relative to one another.

In particular, it is possible to set the specified value or the specified change such that the modulable inertia is different for an acceleration about and/or along different axes, the axes being able to be axes of the reference coordinate system or axes of joints. This can advantageously achieve the effect that undesirable movements of the microscopy system, in particular of the stand, that can arise on account of the kinematic structure of the stand, in particular the concatenation of the individual axes of movement, are hampered or entirely prevented. By way of example, the movement about individual axes can be selectively hampered or facilitated for the user. This advantageously allows the response characteristic of the kinematic structure to be adapted.

In a further exemplary embodiment, a variation in the modulable inertia encodes information for the user. A variation can be for example a periodic variation, or as a further example a harmonic variation, in the modulable inertia. Another form of the change can be an abrupt or ramped increase or decrease in the modulable inertia. This advantageously achieves the effect that information can be output to a user haptically.

In a further exemplary embodiment, selectable values of the modulable inertia and/or a variation, in particular a rate of change, in the modulable inertia is/are limited. In particular, a maximum selectable value and/or a maximum rate of change can be limited, in particular to a predetermined threshold value.

This can advantageously ensure that the sensed inertia of the microscopy system does not change in a surprising manner for the user, since this can otherwise lead to the user becoming irritated. The selectable values or the maximum permissible variation can be determined in advance in this instance, for example in the form of suitable methods for empirical determination.

In a further exemplary embodiment, the specified value or the specified change is determined on the basis of a degree of freedom of movement and/or on the basis of a direction of movement. This determination specific to a degree of freedom of movement and/or specific to a direction of movement has already been explained with applicable advantages above.

In a further exemplary embodiment, an effective inertia and an acceleration of the microscopy system are determined. Furthermore, the effective inertia and the acceleration are taken as a basis for determining an actual value of the modulable inertial force. Furthermore, the at least one drive device is actuated such that a divergence between the actual value of the modulable inertial force and a specified inertial force determined on the basis of the specified value or the specified change is minimized. The actual and specified inertial forces can be directional and/or reference point-oriented forces, as explained above.

It is also possible for such an exemplary embodiment to involve the specified value or the specified change used for determining the specified inertial force not being determined on the basis of the illustrated input variables. As such, the specified value or the specified change can be predetermined in this case. In particular, the specified value or the specified change can be determined such that the specified inertial force corresponds to a predetermined minimum value. Hence, as an independent disclosure, a method for operating a microscopy system including a microscope and a stand for supporting the microscope is described, wherein the microscope is arranged on the stand, wherein the stand includes at least one drive device for moving the microscope. Furthermore, an effective inertia and an acceleration of the microscopy system are determined. Furthermore, the effective inertia and the acceleration are taken as a basis for determining an actual value of the modulable inertial force. Furthermore, the at least one drive device is actuated such that a divergence between the actual value of the modulable inertial force and a predetermined specified inertial force is minimized. The specified inertial force can be determined in particular on the basis of a predetermined specified value or a predetermined specified change of the modulable inertia. This disclosure can be developed in accordance with one or more of the aspect(s) described in this disclosure.

In particular, it is possible to determine the specified value or the specified change such that the specified inertial force is set to a predetermined minimum value. This corresponds to the inertia compensation explained above. In other words, the drive device is actuated such that for the purpose of (in addition to) producing the forces for overcoming friction and attenuation and/or forces for compensating for static weight forces, it also produces forces to compensate for the specified inertial force. If the effective inertia is supposed to be compensated for completely or partially, for example, then the drive device in this case produces a force that assists the user in the desired acceleration of the microscopy system.

In an exemplary embodiment, the effective inertia is determined in model-based fashion. The model can represent in particular a relationship between inertia, in particular also direction specific inertia, and a bearing of the microscopy system. The model can also represent a relationship between the effective inertia, the bearing and the direction of acceleration. The model in this instance can be predetermined. In particular, the model can be determined by suitable methods for system identification or by known calibration methods or by simulation, for example on the basis of CAD data of the microscopy system.

This advantageously results in simple and reliably implementable determination of the effective inertia and hence of the method for operating the microscopy system.

In a further exemplary embodiment, the effective inertia is determined on the basis of a bearing and/or a load. This and corresponding advantages have already been illustrated above.

In a further exemplary embodiment, a specified force is determined for the drive device such that the divergence between the actual value of the modulable inertial force and the specified inertial force is minimized. This likewise advantageously results in simple and reliable implementation of the method for operating the microscopy system.

All in all, the advantageous result is that a modulable inertia of the microscopy system can be adjusted in amplitude and direction in order to assist a user in operating the system and in maintaining safety of operation in various instances of application.

A microscopy system is also provided. The microscopy system in this instance is designed and/or configured such that a method for operating a surgical microscopy system in accordance with one of the exemplary embodiments illustrated in this disclosure is able to be carried out using the microscopy system. The microscopy system is therefore used to carry out such a method.

The microscopy system includes a microscope and a stand for supporting the microscope. The stand includes at least one drive device for moving the microscope. Furthermore, the microscopy system includes at least one control and evaluation device for controlling the operation of the microscopy system.

According to an aspect of the disclosure, the control and evaluation device can be used to determine a specified value or a specified change of a modulable inertia of the microscopy system on the basis of a state variable and/or on the basis of user information and/or on the basis of a force acting on the microscopy system and/or on the basis of a current instance of application, wherein the at least one drive device is controllable such that a divergence between the specified value and an actual value of the modulable inertia is reduced or the modulable inertia is varied in accordance with the specified change.

This advantageously results in a method according to one of the exemplary embodiments explained above being able to be performed using the microscopy system.

Additionally, the microscopy system can include at least one capture device, in particular a sensor, for capturing an input variable or a variable needed for determining the input variable, e.g., a capture device, for example a sensor, for capturing a state variable, user information, a force or a variable needed for determining a desired variable.

Furthermore, the microscopy system can be configured in particular such that the design meets requirements for a human-machine interface (HMI). These requirements can result from a suitability for the task, a self-explanatory nature, a controllability, a conformance to expectations, an error robustness, an adaptability/teachability of the system, for example. A suitability for the task is ensured in particular by virtue of the determination of the specified value or of the specified change illustrated above being adapted to a use context, in particular the instances of application illustrated above. Error robustness can mean in particular that the system can be operated in stable fashion and/or in a manner adapted to a user feeling even with the proposed determination of the specified value or the specified change. The system exhibits teachability and a self-explanatory nature in particular if the microscopy system behaves in a manner predictable by the user.

Figure 10:
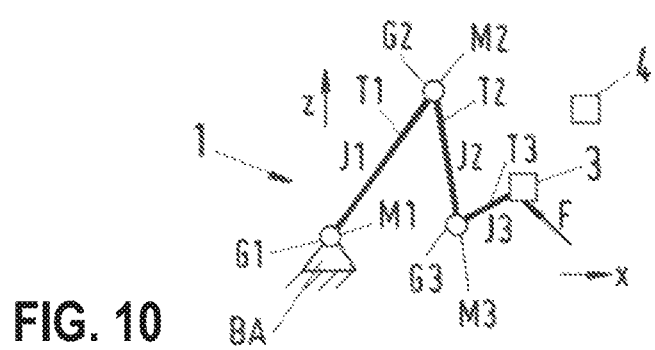
FIG. 10 shows a schematic depiction of a microscopy system according to a first exemplary embodiment of the disclosure.

FIG. 1 depicts a schematic flowchart of a method according to an aspect of the disclosure for operating a microscopy system 1 (see FIG. 10). In a first step S1, at least one input variable E is determined. It is possible that precisely one input variable E is determined or that multiple instances of the input variables E illustrated in even more detail below are determined in the first step S1. An input variable E can be a movement variable of the microscopy system 1, in particular. A movement variable in this instance can be a jerk, an acceleration, a speed or a spatial bearing, that is to say a spatial position and/or spatial orientation. A further movement variable can be a relative position of two parts T1, T2, and T3 (see FIG. 10) of the microscopy system 1, in particular of a stand of the microscopy system 1, that are mobile relative to one another about or along a joint G1, G2, and G3, the subsections T1, T2, and T3 being mechanically connected to one another via the joint G1, G2, and G3.

These movement variables can have a direction and an amplitude. The input variables in this instance can be referenced to one of the coordinate systems illustrated above. Furthermore, these input variables can be referenced to a reference point and/or a reference axis of the microscopy system 1, for example an interaction point, a focal point, a center of gravity or another reference point and/or an axis of a joint of the microscopy system 1, an optical axis or another axis.

A further input variable E can be a force F acting on the microscopy system (see FIG. 10) or a moment acting on the microscopy system 1. Such an input variable E can also have an amplitude and a direction. Furthermore, the input variable E can likewise be referenced to one of the reference points illustrated above and one of the coordinate systems illustrated above. A force F acting on the microscopy system 1 in this instance can be a force applied by a user, for example, in particular a force for moving or positioning the microscopy system 1. A force F acting on the microscopy system can also be a force resulting from a load. If the microscopy system 1 is a balanced microscopy system 1, then the force resulting from a load is compensated for by the balancing.

An input variable E can also be user information. User information can be in particular a user property or a mode of user action. Furthermore, an input variable E can be an operating parameter set selected for operation, which can be a user specific parameter set, in particular.

An input variable can also be information about a current instance of application, e.g., information about a surgical or movement phase that the microscopy system 1 is currently in.

The precisely one or the multiple input variables E are used in a second step S2 in order to determine an output variable A on the basis of the at least one input variable E. The output variable A in this instance can be a specified value or a specified change of a modulable inertia of the microscopy 1. The modulable inertia in this instance has been explained above. If the output variable A is a specified value, then an amplitude or an absolute value of the specified value can be determined in the second step S2. If the output variable A is a specified change, then an arithmetic sign of the specified change can be determined in the second step S2, with, e.g., the modulable inertia being increased for a positive arithmetic sign and the modulable inertia being decreased for a negative arithmetic sign. The rate of change of the specified change can also be determined. It is possible, but not imperative, that an absolute value of the specified change is also determined.

It is also possible that a specified value is determined on the basis of a specified change, in particular if an arithmetic sign of the change and an absolute value of the specified change are determined. A specified change can also be determined on the basis of a specified value.

It is furthermore possible that a direction of the output variable is also determined. As such, the output variable A can also be referenced to one of the reference points illustrated above and one of the coordinate systems illustrated above. However, it is also possible to determine the output variable independently of direction, that is to say in particular even without direction information.

In a third step, at least one drive device M, M1, M2, and M3 (see, e.g., FIG. 9 and FIG. 10) of the stand is then controlled by open-loop or closed-loop control such that a divergence between the specified value and an actual value of the modulable inertia is reduced, typically to a predetermined minimum value, which is lower than a predetermined threshold value. If the output variable A determined is a specified change of the modulable inertia, then the at least one drive device M, M3 is controlled such that the modulable inertia is varied in accordance with the specified change.

In the third step S3, methods for open-loop or closed-loop control that are known to a person skilled in the art can be used.

FIG. 2 shows a schematic flowchart of a method according to a further exemplary embodiment of the disclosure.

A first step in this instance corresponds to the first step of the exemplary embodiment depicted in FIG. 1. In a first substep S2a of a second step S2, precisely one of the input variables E illustrated above or a set comprising multiple instances of the input variables E illustrated above is then taken as a basis for classifying an instance of application AF. Such an instance of application can be, e.g., a movement phase of the movement of the microscopy system 1 by a user. Such a movement phase can be in particular a phase of positive acceleration, a phase of continuous movement, which can also be referred to as a phase of uniform movement, or a phase of negative acceleration. A movement phase can also be a coarse positioning phase or a fine positioning phase.

It is possible that the instance of application is additionally determined on the basis of at least one further variable in the first substep S2a of the second step S2, the further variable not forming an input variable E. By way of example, such a further variable can be an output signal of a device or of a system for optically capturing the user. A further variable can also be information about a user input that is input via an input device, for example a haptic or audible user input. A further variable can also be a variable that describes patterns of operation, for example movement patterns. The pattern in this instance can be a user specific pattern.

An instance of application, in particular a movement phase, in this instance can be classified using classification methods known to a person skilled in the art. Known classification methods include for example evaluation of predetermined relationships, for example in the form of lookup tables, evaluation of previously known functional relationships, e.g., of characteristic curves, classification with neural networks or artificial intelligence methods, classification with Markov processes, or else other known classification methods.

The output variable A illustrated above can then be determined on the basis of the instance of application AF in a second substep S2b of the second step S2. A third step S3 in this instance corresponds to the third step S3 of the exemplary embodiment depicted in FIG. 1.

FIG. 3 shows a schematic flowchart of a method according to a further exemplary embodiment of the disclosure. In this instance, a first and a third step S1 and S3 of the method depicted in FIG. 3 correspond to the first and third steps S1 and S3 of the method depicted in FIG. 1. In a first substep S2a of a second step S2 of the method, precisely one input variable E or a set comprising multiple input variables E is taken as a basis for determining user information NI. The user information NI can be in particular a user interaction modality, a user property or a user specific operating parameter set. It is possible that the user information NI is taken as a basis for determining an instance of application AF (see FIG. 2).

It is possible that—as also explained for the exemplary embodiment depicted in FIG. 2—the user information NI is additionally determined on the basis of at least one further variable in the first substep S2a of the second step S2, the further variable not forming an input variable E.

It is therefore possible to determine user information likewise using one or more of the classification methods illustrated above. Of course, it is possible for this to involve the classification method being performed by evaluating data that were determined during preceding operation, for example. These data may be stored, for example.

Furthermore, the output variable A illustrated above can be determined on the basis of the user information NI in a second substep S2b of the second step S2.

FIG. 4 shows a schematic flowchart of a method according to a further exemplary embodiment of the disclosure. In a first substep S1a of a first step S1, a first input variable E1 or a first set including multiple input variables E1 is determined. In a first substep S2a of a second step S2, this first input variable E1 or set of input variables E1 is taken as a basis for determining a first output variable A1, which can be a subvariable of a resulting output variable A. The first substep S2a in this instance can correspond to the second step S2 depicted in FIG. 1, FIG. 2 or FIG. 3.

In a further substep S1b of the first step S1 of the method depicted in FIG. 4, a further input variable E2 or a set comprising multiple further input variables E2 is determined. In this instance, at least one of the input variables E2 determined in the second substep S1b can be different than the at least one input variable E1 determined in the first substep S1a. In a second substep S2b of the second step S1, the further input variable(s) E2 is/are taken as a basis for determining a second output variable A2, which can be a further subvariable of a resulting output variable A. This second substep S2b can also correspond to the second step S2 depicted in FIG. 1, FIG. 2, or FIG. 3. In a third substep S2c of the second step S2 of the method depicted in FIG. 4, the output variables A1 and A2 are then taken as a basis for determining a resulting output variable A. This can be accomplished using methods known to a person skilled in the art for determining a resulting variable from multiple subvariables, for example fusion methods. Such a method can include averaging, for example. The third step S3 of the method depicted in FIG. 4 can correspond to the third step of the method depicted in FIG. 1.

Figure 5:
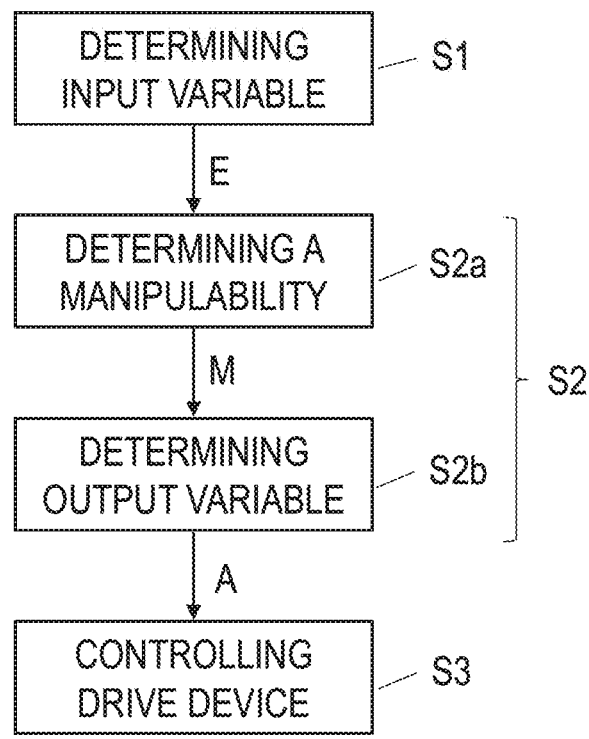
FIG. 5 shows a schematic flowchart of a method according to a further exemplary embodiment of the disclosure.

FIG. 5 shows a schematic flowchart of a method according to a further exemplary embodiment of the disclosure. In this instance, a first step S1 and a third step S3 of the method depicted in FIG. 5 correspond to the first and third steps S1 and S3 depicted in FIG. 1.

In a first substep S2a of a second step S2, the at least one input variable E is taken as a basis for determining a manipulability M of the microscopy system 1 (see FIG. 10). The manipulability M is then taken as a basis for determining an output variable A in a second substep S2b. This has already been illustrated in more detail in the general part of the description.

Figure 6:
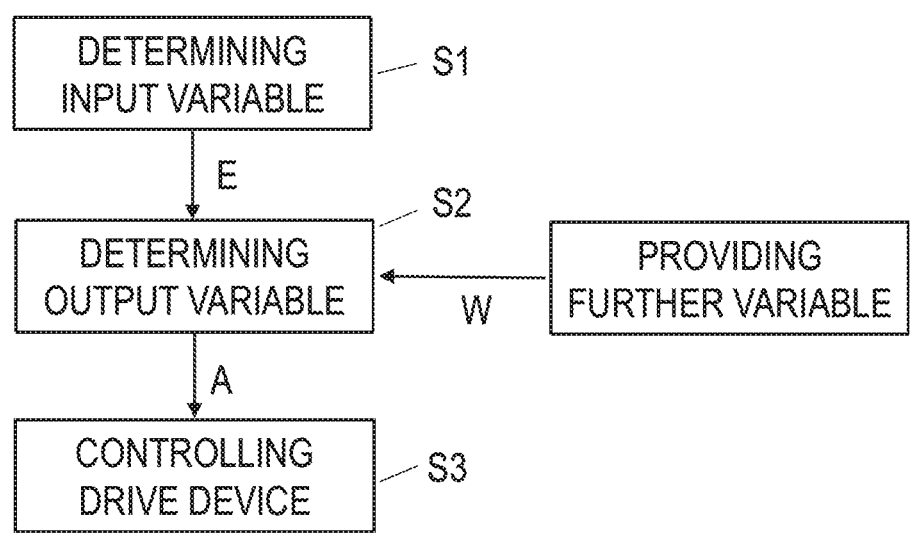
FIG. 6 shows a schematic flowchart of a method according to a further exemplary embodiment of the disclosure.

FIG. 6 shows a schematic flowchart of a method according to a further exemplary embodiment of the disclosure. In this instance, a first and a third step S1 and S3 of the method depicted in FIG. 6 can correspond to a first and a third step S1 and S3 of the method depicted in FIG. 1. In a second step S2, an output variable A is determined on the basis of the at least one input variable E and a further variable W, the further variable W not corresponding to any of the input variables E illustrated above. As such, by way of example, it is possible that the at least one input variable E is taken as a basis for determining an actual direction of movement of the microscopy system. The further variable W can be taken as a basis for determining a specified direction of movement. The further variable W can also represent this specified direction of movement. However, it is also possible that the specified direction of movement is determined on the basis of the at least one input variable E.

All in all, it is possible that an actual value of the modulable inertia is determined on the basis of the at least one input variable E, in particular in model-based fashion. This is illustrated in even more detail below.

Furthermore, it is also possible that the output variable A is an axis specific output variable, in particular if the microscopy system 1 (see FIG. 10) has multiple axes about or along which parts T1, T2, and T3 of the microscopy system 1 can be moved relative to one another. It is also possible that the output variable A encodes user information.

Of course, it is also conceivable that the output variable A is restricted, for example to a maximum permissible value and/or to a minimum permissible value.

It is also possible that the output variable A is determined in a manner specific to the degree of freedom of movement or in a manner specific to the direction of movement or in a manner specific to the bearing.

Figure 7:
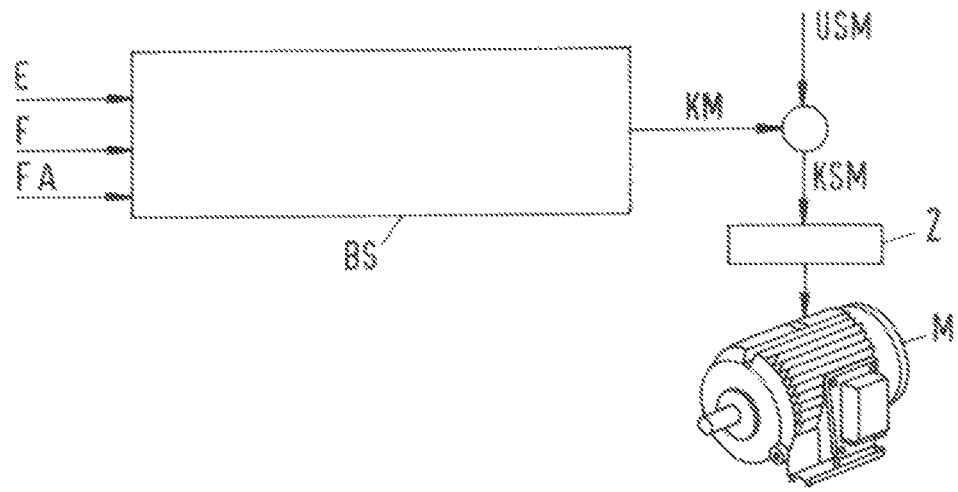
FIG. 7 shows a schematic block diagram for visualizing a method according to a further exemplary embodiment of the disclosure.

FIG. 7 shows an exemplary block diagram for visualizing a method according to an aspect of the disclosure, in particular in which form a drive device M is controllable.

The moment-oriented illustrations provided below for a drive device M that can produce a torque also apply accordingly to forces, e.g., that is to say including to a drive device that can provide a force, in this instance.

In particular, an unmodified specified moment USM for the drive device M can be varied in order to form a modified specified moment KSM.

This accordingly varied or modified specified moment KSM then forms an input variable for a closed-loop control device 2 for operating the drive device M. It is possible that the unmodified specified moment USM is varied such that the force needing to be applied by a user in order to overcome the inertia of the microscopy system 1, in particular in order to overcome it completely or overcome it proportionally, is produced by the drive device M.

If the modified specified moment KSM is determined such that the force needing to be applied by the user in order to overcome the inertia is provided completely or almost completely by the drive device M, then the modified specified moment can also be referred to as compensated specified moment.

To determine the modified specified moment, a modification moment KM can be determined in a determination step BS. The modification moment KM can be determined in particular on the basis of an input variable E, in particular on the basis of the acceleration, of the microscopy system 1. By way of example, the modification moment KM can be determined in model based fashion, wherein the model MM (see FIG. 8) describes the effective inertia EJ of the microscopy system 1 (see FIG. 10) and therefore allows determination of an actual value of an inertial force that the user needs to apply in order to accelerate the microscopy system 1 as desired. On the basis of this force to be applied, the modification moment KM can then be determined, in particular after appropriate coordinate transformation, such that this force is varied, in particular reduced, furthermore in particular completely or proportionally. In this instance, the type of variation, the level of the variation and/or a rate of change is obtained from the output variable illustrated above.

In this instance, it is possible that the effective inertia EJ of the microscopy system 1 is determined on the basis of a bearing of the microscopy system 1 in space. The bearing can be determined in particular on the basis of movement variables, in particular a relative position of parts T1, T2, and T3 (see FIG. 10) that are mobile relative to one another.

Alternatively or cumulatively, the effective inertia EJ can be determined on the basis of a force F acting on the microscopy system, in particular the force resulting from a load and/or the force F applied by the user in order to move the microscopy system 1. This force can be determined with a force sensor, for example.

Furthermore, in this case it is possible to determine the effective inertia or the actual value of the modulable inertial force on the basis of the force FA transferred to a floor area via the microscopy system 1 or the force FA exerted on the floor area by the microscopy system 1. The floor area in this instance can be a surface of the floor or of a foundation that the microscopy system 1, in particular the stand, is standing on. The force FA transferred to the floor area or the force FA exerted on the floor area by the microscopy system 1 can be measured, e.g., with a force sensor. This allows the inertia-induced proportion of the force F applied by the user to be determined more accurately, in particular on the basis of or as a difference between the force FA applied by the user and the force FA exerted on the floor area.

It is also conceivable that the forces acting in the joints are determined, e.g., with force sensors, wherein the effective inertia or the actual value of the modulable inertial force are determined on the basis of these forces, in particular on the basis of or as a difference between the force FA applied by the user and the forces determined in the joints or a resulting force determined from these forces.

As a further alternative, it is possible to determine the effective inertia or the actual value of the modulable inertial force on the basis of the force F exerted by the user or the force FA exerted on the floor area or the forces determined in the joints using a dynamic model of the microscopy system 1. In this case, one of the aforementioned forces/sets of forces can suffice in order to determine the effective inertia or the actual value of the modulable inertial force.

Figure 8:
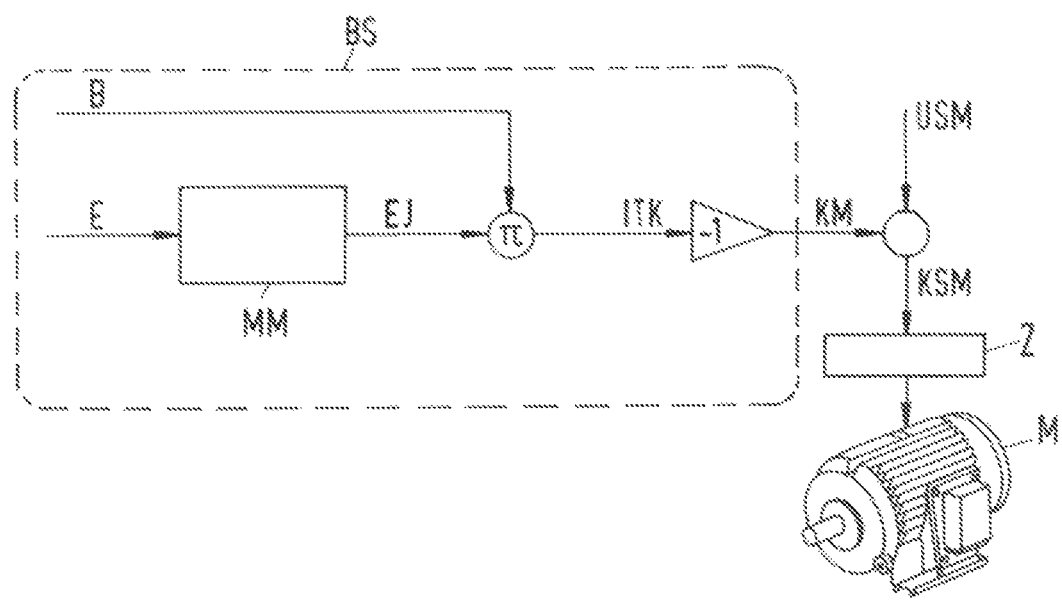
FIG. 8 shows a schematic block diagram for visualizing a method according to a further exemplary embodiment of the disclosure.

FIG. 8 shows a schematic block diagram for visualizing a method according to a further exemplary embodiment of the disclosure, in particular for completely compensating for an inertial force.

In this instance, an effective inertia EJ of the microscopy system 1 is determined in model-based fashion, in particular with a predetermined model MM of the microscopy system 1 (see FIG. 10). This effective inertia EJ can be determined in particular on the basis of at least one input variable E, in particular on the basis of a load and/or a bearing of the microscopy system 1 in space.

Furthermore, at least one acceleration B of the microscopy system 1 is determined.

The acceleration B and the effective inertia EJ can then be taken as a basis for determining an actual inertial force ITK of the microscopy system 1 with a multiplication operation π. The actual value of this modulable inertia ITK can then be taken as a basis for minimizing a divergence between the actual inertial force and a specified inertial force determined on the basis of the specified value illustrated above or the specified change.

In this instance, FIG. 8 depicts that the specified inertial force corresponds to a predetermined minimum value and hence the actual inertial force ITK is supposed to be reduced by superimposing the modification moment KM. In other words, a user is supposed to exert a very small force in order to overcome the inertia of the microscopy system 1 during acceleration. This modification moment KM determined in this manner can then, as illustrated above, be superimposed on an unmodified specified moment USM of a drive device M in order to form a modified specified moment KSM. This in turn can be used as input variable for a closed-loop control device 2 for operating the drive device M.

Figure 9:
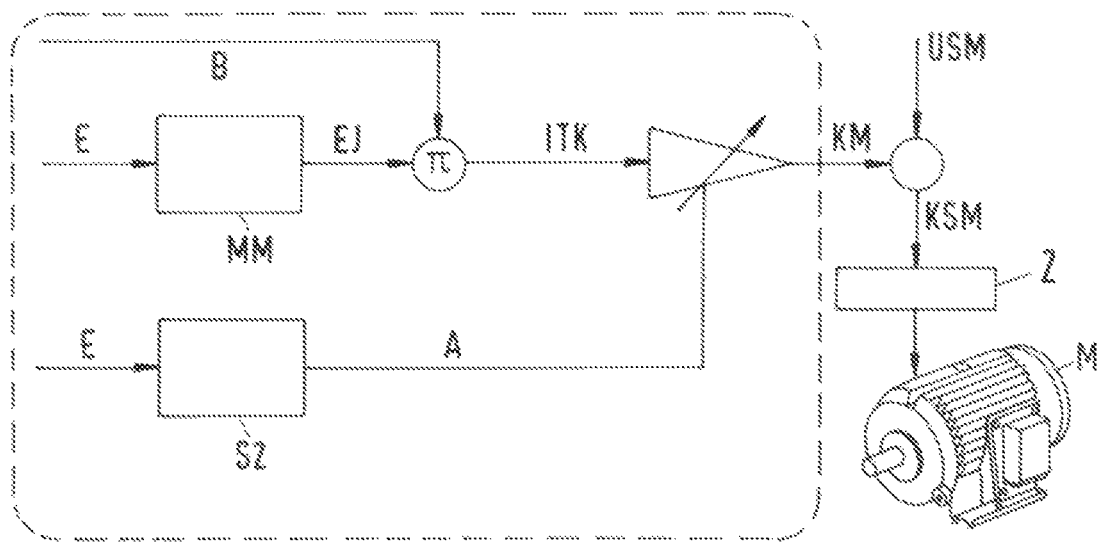
FIG. 9 shows a schematic block diagram for visualizing a method according to a further exemplary embodiment of the disclosure.

FIG. 9 shows a schematic block diagram for visualizing a method according to a further exemplary embodiment of the disclosure.

In addition to the determination of the modification moment KM depicted in FIG. 8, an output variable A is determined, e.g., as depicted in FIGS. 1 to 6, on the basis of at least one input variable E, which represents a specified value or a specified change of the modulable inertia. In particular, the output variable A can be taken as a basis for determining a specified inertial force that the user is supposed to overcome when operating, in particular accelerating, the microscopy system 1. This actual inertial force ITK and the specified inertial force can then be taken as a basis for determining the modification moment KM, in particular such that the divergence between the actual and specified inertial forces is reduced.

The modified specified moment KSM as input variable for the closed-loop control device 2 of the drive device M can then be determined as above already in association with the embodiments depicted in FIG. 7 and FIG. 8.

FIG. 10 schematically shows a microscopy system 1 having a microscope 2, a control device 4, and a stand, which includes multiple parts T1, T2, and T3 that are mobile relative to one another, the parts T1, T2, and T3 that are mobile relative to one another being connected to one another or to a base section BA via joints G1, G2, and G3.

The microscopy system 1 in this instance can include the base section BA. The base section BA in this instance can be arranged at a fixed location in a normal mode of the microscopy system 1. However, this does not preclude a bearing of the base section from being able to be varied, in particular outside of a normal mode.

Purely as an example, rotary joints are depicted in FIG. 10. Of course, the joints can also be configured as linear joints, however. Inertias J1, J2, and J3 associated with the individual mobile parts T1, T2, and T3 are also schematically depicted. These inertias represent inertias that counter a movement, in particular about a predetermined axis. Drive devices M1, M2, and M3 that can cause or drive a rotational movement about the illustrated joints G1, G2, and G3 are also depicted.

A force F acting on the microscopy system 1 is also depicted, this force F also being able to symbolize a moment acting on the microscopy system 1. This can be a force F applied by the user, for example. The user in this instance can apply this force F via handles, not depicted, for example, which can be part of the stand or part of the microscope 3.

The proposed method can be used to determine the specified value or the specified change of the modulable inertia in axis specific fashion. By way of example, a proportion of the modulable inertia formed by the inertia of the first moving part T1 can be increased, with the proportions of the modulable inertia formed by the inertias of the second and third mobile parts T2 and T3 remaining constant or being decreased. The effect that can be achieved by this is that the microscopy system 1 facilitates the movement about the second and third joint G2 and G3 for itself when operated by the user, for example as a result of application of the depicted force F, with a movement about the first joint G1 being hampered. Corresponding remarks apply, of course, when proportions of the modulable inertia formed by the inertia of the second part T2 of the third part T3 are varied.

A reference coordinate system with a vertical axis z and a longitudinal axis x is also depicted as an example. The vertical axis z in this instance is oriented parallel to a gravitational force and counter thereto. The longitudinal axis x in this instance is oriented perpendicularly with respect to the vertical axis and perpendicularly with respect to a transverse axis y, not depicted, which is oriented perpendicularly with respect to the plane of the drawing in FIG. 10 and away from the viewer.

The proposed method, which is executed by the control device 4, can also be used to determine the specified value or the specified change of the modulable inertia in a manner specific to the direction of movement or in a manner specific to the degree of freedom of movement, for example for a movement/acceleration along the axes x, y, and z and/or about the axes x, y, and z.

Figure 11:
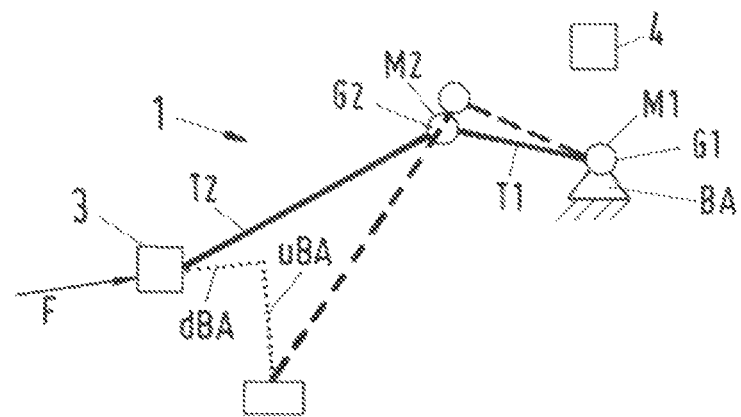
FIG. 11 shows a schematic block diagram of a microscopy system according to a further exemplary embodiment of the disclosure.

FIG. 11 shows a schematic depiction of a microscopy system in accordance with a further exemplary embodiment. Two mobile parts T1 and T2 and a base section BA of a stand of the microscopy system 1 are depicted in this instance, the first mobile subsection T1 being mounted about a rotary joint G1 on the base section BA. The second subsection T2 is mounted on the first subsection T1 via a second rotary joint G2. Drive devices M1 and M2 that can cause or drive a rotational movement about the illustrated joints G1 and G2 are also depicted. A microscope 3 of the microscopy system 1, which is arranged on the stand, is likewise depicted.

A force F exerted on the microscopy system 1 by a user, for example on handles arranged on the stand or on the microscope 3, is also depicted. Dashed lines depict a bearing of the microscopy system 1 that is obtained without a variation in the modulable inertia, that is to say when the effective inertia is unaltered, when a movement of the microscopy system 1 resulting from the force F is performed. A desired movement component dBA and an undesirable movement component uBA are depicted in this instance. The desired movement component dBA in this instance corresponds to a movement in the direction of the force F applied by the user.

The method according to an aspect of the disclosure allows the modulable inertia of the microscopy system 1 to be adapted such that a modulable inertia of the microscopy system is increased for accelerations B (see FIG. 9) whose direction diverges from the desired direction of movement to more than a predetermined extent, whereas a modulable inertia is decreased for accelerations B that diverge from the desired direction of movement less than or to the predetermined extent.

The modulable inertia can also be adapted in a manner specific to the movement component, wherein the modulable inertia is set to be higher for a movement component of the actual direction of movement whose direction is different than the specified direction of movement than for a movement component of the actual direction of movement whose direction corresponds to the specified direction of movement.

It is understood that the foregoing description is that of the exemplary embodiments of the disclosure and that various changes and modifications may be made thereto without departing from the spirit and scope of the disclosure as defined in the appended claims.

What is claimed is:

1. A method for operating a microscopy system including a microscope and a stand for supporting the microscope, the microscope being arranged on the stand, the stand including at least one actuator for moving the microscope, the method comprising:
   determining a specified value of a modulable inertia or a specified change of the modulable inertia of the microscopy system based on at least one of:
      a state variable of the microscopy system, wherein the state variable represents an operating state of the microscopy system,
      information about a user of the microscopy system, wherein the information about the user of the microscopy system represents at least one of a user interaction modality, a user property, and a user specific operating parameter set,
      a force acting on the microscopy system, and
      a value representing a current instance of application, wherein the current instance of application defines at least one of a scenario in which the microscopy system is operated, a phase of operation of the microscope within the scenario, and a phase of movement of the microscope within the scenario; and
   controlling the at least one actuator such that a divergence between the specified value of the modulable inertia and an actual value of the modulable inertia is reduced or such that the modulable inertia is varied in accordance with the specified change of the modulable inertia of the microscopy system,
   wherein the modulable inertia is inertia perceived by the user with the microscopy system is simultaneously accelerated by the user and by the at least one actuator, wherein the modulable inertia is adjustable by the controlling of the at least one actuator based on the specified value or the specified change,
wherein the modulable inertia correlates with or results in a force which the user must apply to accelerate the microscopy system, and
wherein the modulable inertia is set such that acceleration in different directions requires different forces.

2. The method as claimed in claim 1, further comprising:
determining the specified value or the specified change based on at least one of:
an acceleration,
a speed of movement,
a jerk,
a current spatial bearing, and
a value representing a current relative position of parts of the microscopy system that are mobile relative to one another.

3. The method as claimed in claim 1, further comprising:
determining a manipulability or a variation in the manipulability, and
determining the specified value or the specified change based on the manipulability or the variation therein.

4. The method as claimed in claim 1, further comprising:
determining a specified direction of movement and an actual direction of movement, and
determining the specified value or the specified change based on a divergence between the specified and actual directions of movement.

5. The method as claimed in claim 1, further comprising:
determining a movement phase of a movement of the microscopy system, and
determining the specified value or the specified change based on the movement phase.

6. The method as claimed in claim 5, further comprising:
setting the specified value or the specified change based on a duration of the movement phase.

7. The method as claimed in claim 1, further comprising:
determining the specified value or the specified change based on at least one of:
at least one user property, wherein the at least one user property represents at least one of (a) a bearing of the user relative to the microscopy system, (b) an anatomical or physiological property of the user, and (c) a user condition, wherein the anatomical or physiological property of the user includes a height of the user, and wherein the user condition includes a level of fatigue, a level of ability to concentrate, and a level of exhaustion,
a selected operating parameter set, wherein the selected operating parameter set includes parameters for operating the microscopy system,
a mode of user interaction, wherein the mode of user interaction defines how the user interacts with the microscopy system, and
a detected movement pattern.

8. The method as claimed in claim 1, further comprising:
determining a load of the microscopy system, and
determining the specified value or the specified change based on the load.

9. The method as claimed in claim 1, wherein:
the microscopy system is movable about and/or along a first axis and about and/or along at least one further axis, and
the method further comprises setting the specified value or the specified change depending on at least one of the first axis and the at least one further axis.

10. The method as claimed in claim 1, wherein a variation in the modulable inertia encodes information for the user which is encoded by a change of inertia which allows the information to be haptically output to the user.

11. The method as claimed in claim 1, wherein selectable values of the modulable inertia and/or a variation in the modulable inertia is/are limited by limiting a maximum selectable value of the modulable inertia and/or a maximum rate of change to a predetermined threshold value.

12. The method as claimed in claim 1, further comprising:
determining the specified value or the specified change based on at least one of:
a degree of freedom of movement, and
a direction of movement.

13. The method as claimed in claim 1, further comprising:
determining an effective inertia and an acceleration,
taking the effective inertia and the acceleration as a basis for determining the actual value of a modulable inertial force,
actuating the at least one actuator such that the divergence between the actual value and a specified inertial force determined based on the specified value or the specified change is minimized.

14. The method as claimed in claim 13, further comprising:
determining the effective inertia based on a model, wherein the model represents a relationship between inertia and a bearing of the microscopy system.

15. The method as claimed in claim 13, further comprising:
determining the effective inertia based on at least one of a position and a load.

16. The method as claimed in claim 13, further comprising:
determining a specified force for the at least one actuator such that the divergence between the actual value and the specified inertial force is minimized.

17. The method as claimed in claim 1, wherein the state variable is an optical variable,
wherein a value of the optical variable represents a selected magnification of the microscope or a selected focal distance of the microscope,
wherein the user property represents at least one of (a) a bearing of the user relative to the microscopy system, (b) an anatomical or physiological property of the user, and (c) a user condition,
wherein the anatomical or physiological property of the user includes a height of the user,
wherein the user condition includes a level of fatigue, a level of ability to concentrate, and a level of exhaustion,
wherein the value representing the current instance of application represents a surgical phase, and
wherein the surgical phase is a preoperative phase, an intraoperative phase, or a post-operative phase.

18. A microscopy system comprising:
a microscope,
a stand supporting the microscope and including at least one actuator configured to move the microscope,
at least one controller configured to control an operation of the microscopy system,
the at least one controller being configured to:
determine a specified value of a modulable inertia or a specified change of a modulable inertia of the microscopy system based on at least one of:
a state variable, wherein the state variable represents an operating state of the microscopy system, information about a user of the microscopy system, wherein the information about the user of the microscopy system represents a user interaction modality, a user property, or a user specific operating parameter set, a force acting on the microscopy system, and a value representing a current instance of application, wherein the current instance of application defines at least one of a scenario in which the microscopy system is operated, a phase of operation of the microscope within the scenario, and a phase of movement of the microscope within the scenario, wherein the at least one actuator is controllable such that a divergence between the specified value of the modulable inertia and an actual value of the modulable inertia is reduced or such that the modulable inertia is varied in accordance with the specified change of the modulable inertia of the microscopy system, wherein the modulable inertia is inertia perceived by the user with the microscopy system is simultaneously accelerated by the user and by the at least one actuator, wherein the modulable inertia is adjustable by controlling the at least one actuator based on the specified value or the specified change, wherein the modulable inertia correlates with or results in a force which the user must apply to accelerate the microscopy system, and wherein the modulable inertia is set such that acceleration in different directions requires different forces.

* * * * *